US006146833A

United States Patent [19]
Milton

[11] Patent Number: 6,146,833
[45] Date of Patent: Nov. 14, 2000

[54] POLYMERIC REAGENTS FOR IMMOBILIZING BIOPOLYMERS

[75] Inventor: Raymond C. Milton, La Habra, Calif.

[73] Assignee: Beckman Coulter, Inc., Fullerton, Calif.

[21] Appl. No.: 09/347,958

[22] Filed: Jul. 6, 1999

Related U.S. Application Data

[63] Continuation-in-part of application No. 08/797,222, Feb. 11, 1997.

[51] Int. Cl.[7] .............................. C12Q 1/68; C12Q 1/70; C12P 19/34; C07H 19/00; C07H 21/02
[52] U.S. Cl. .................. 435/6; 435/5; 435/91.1; 435/91.2; 536/22.1; 536/23.1
[58] Field of Search .................. 435/5, 6, 91.1, 435/91.2; 536/22.1, 23.1

[56] References Cited

U.S. PATENT DOCUMENTS

| | | | |
|---|---|---|---|
| 4,264,750 | 4/1981 | Anand et al. | 525/356 |
| 4,749,414 | 6/1988 | Wu et al. | 106/183 |
| 4,780,504 | 10/1988 | Buendia et al. | 525/54.11 |
| 5,011,861 | 4/1991 | Coull et al. | 521/53 |
| 5,098,960 | 3/1992 | Frautschi | 525/359.3 |
| 5,360,928 | 11/1994 | Carpino et al. | 562/849 |
| 5,424,186 | 6/1995 | Fodor et al. | 435/6 |
| 5,554,501 | 9/1996 | Coassin et al. | 435/6 |

FOREIGN PATENT DOCUMENTS

| | | |
|---|---|---|
| 0301932 | 2/1989 | European Pat. Off. . |
| 0318115 | 5/1989 | European Pat. Off. . |
| 1347947 | 11/1963 | France . |
| 1595194 | 4/1970 | Germany . |
| 980160A | 1/1965 | United Kingdom . |
| WO 92/07864 | 5/1992 | WIPO .............. C07H 15/12 |
| WO 92/07882 | 5/1992 | WIPO . |

OTHER PUBLICATIONS

Gardner et al. *Journal of the American Chemical Society*, vol. 75, pp. 246–248, Jan. 5, 1993.

Jedrzejczak, Maria et al; "The Kinetics of Aminolysis of Acyl Halides"; *J. Chem. Soc. Perkin Trans. 2*; pp. 599–600; 1993.

Carpino, Louis A. et al; "Peptide Synthesis via Amino Acid Halides"; *Acc. Chem. Res.*; 2996, 29, pp. 268–274, 1996.

Satchell, D. P. N.; "Acylation. Part VIII. The Mechanism of the Acid–catalysed Solvolysis of Acyl Derivatives: the Fluorides as a Special Case? Pp. 555–569", 1963.

Motie, Richard E. et al; "The Bronsted Acid–catalysed Hydrolysis of Acyl Fluorides in Aqueous Media"; *J. chem. Soc. Perkin Trans. 2* 1993; pp. 1087–1090.

(List continued on next page.)

*Primary Examiner*—Jezia Riley
*Attorney, Agent, or Firm*—William H. May; Margaret A. Kivinski

[57] ABSTRACT

Reagents for the immobilization of biopolymers, processes for their preparation and their subsequent use in the immobilization of biopolymers for analytical and diagnostic procedures are described. One type of reagent includes a solid support fabricated of a polymeric material having at least one surface with pendant acyl fluoride functionalities. Another reagent includes solid supports fabricated of polymeric materials including ethylene acrylic acid or ethylene methacrylic acid copolymers and activated polypropylene. Processes for preparing reagents include derivatizing polymeric materials to form acyl fluoride functionalities or derivatizing ethylene acrylic acid copolymers and ethylene methacrylic acid copolymers to form active acyl functionalities. Processes for immobilizing biopolymers include attaching natural or presynthesized biopolymers to activated solid support surfaces and directly attaching in a step-wise successive manner biomonomer units to a growing biopolymer chain attached to the solid support reagent.

14 Claims, 18 Drawing Sheets

OTHER PUBLICATIONS

Motie, Richard E., et al; "The Bronsted Acid–catalysed Hydrolysis of Acyl Fluorides in Aqueous Media; Evidence for Two Mechanisms"; *J. Chem. Soc. Perkin Trans. 2* 1992; pp. 859–860.

Miller, Joseph, et al; "Halogen Mobility in $S_n2$ Reactions of Carbonyl Compounds. Comparisons with Aromatic Halogen Mobility"; *J. Chem. Soc. Perkin Trans. II* 1985; pp, 323–327.

Satchell, D.P. N. et al; "Mechanistic aspects. Recent Developments Concerning Mechanisms of Aaacylation by Carboxylic Acid Derivatives" *Supplement B: The Chemistry of Acid Derivatives*, vol. 2 1992, pp. 747–803.

Matson, R., et al; Biopolymer Synthesis on polypropylene Supports: Oligonucleotide Arrays; *Analytical Biochemistry 224*, 110–116 (1995).

Wehnert, Manfred S., et al; A rapid scanning strip for tri– and dinucleotide short tandem repeats; *Nucleic Acids Research,* 1994, vol 22, No. 9, 1701–1704.

Hudlicky, Milos; Chapter 3, "Fluorination with Diethylaminosulfur Trifluoride and Related Aminofluorosulfuranes"; *Organic Reactions 35,* 513–637 (1988).

Carpino, Louis A., et al; (9–Fluorenylmethyl)oxy)carbonyl (FMOC) Amino Acid Fluorides, Convenient New Peptide Coupling Reagents Applicable to the FMOC/tert–Butyl Strategy for Solution and Solid–Phase Syntheses; *J. American Chemical Society* 1990, 112, 9651–9652.

Gait, M. J.; Oligonucleotide Synthesis—a practical approach; *MCR Laboratory of Molecular Biology* 1984 p. 11–17.

Nakajima, K., et al; Adsorption of Plasma Proteins on Arg–Gly–Asp–Ser Peptide–Immobilized Poly(vinyl alcohol) and Ethylene–Acrylic Acid Copolymer Films; *Polymer Journal,* vol. 22, No. 11, pp. 985–990 (1990).

Englebretsen et al; "High Yield, Directed Immobilization of a Peptide–Ligand Onto a Cellulose Suport"; Peptide Research, vol. 7, pp. 322–326, 1994.

March "Advanced Organic Chemistry" Third Edition, A Wiley–Interscience Publication, John Wiley & Sons, New York, p. 388, 1985.

Chemical Abstracts, vol. 113, No. 20, Nov. 20, 1990, abstract No. 173002g, p. 19 and JP 02 170 801 A; 7/1/990.

Activated Nucrel #1202HC ethylene methacrylic acid film substrate [FOC-ethylene methacrylic acid]

Activated Primacor #3460 ethylene acrylic acid molded substrate [FOC-ethylene acrylic acid]

Activated, carbon black-impregnated, Nucrel #0903 ethylene methacrylic acid molded substrate
[FOC-ethylene methacrylic acid]

Thermal inkjet printed genosensor array on activated plasma-aminated polypropylene substrate
[FOC(CH2)2CONH-polypropylene]

H-ras wlt target

H-ras wlt probe

H-ras wlt probe

Thermal inkjet printed genosensor array on activated Nucrel #0910 ethylene methacrylic acid molded substrate [FOC-ethylene methacrylic acid]

Mixture of all five target sequences

Activated, plasma-aminated polypropylene film substrate
[FOC(CH2)2CONH-polypropylene]

H-ras w/t target

Activated, plasma-aminated polypropylene film substrate [FOC(CH2)2CONH-polypropylene]

Poly-T target

Activated, plasma-aminated polypropylene film substrate [FOC(CH2)2CONH-polypropylene]

K-ras w/t target

Activated, plasma-aminated polypropylene film substrate
[FOC(CH2)2CONH-polypropylene]

POLYMERIC REAGENTS FOR IMMOBILIZING BIOPOLYMERS

This is a Continuation-in-Part application of U.S. patent application Ser. No. 08/797,222, filed on Feb. 11, 1997.

BACKGROUND OF THE INVENTION

1. Field of the Invention

The present invention generally involves polymeric materials and methods of using the polymeric materials for immobilizing biopolymers. More particularly, the present invention relates to activated polymeric films and molded parts, methods for preparing activated polymeric films and molded parts and methods for immobilizing biopolymers onto activated polymeric films and molded parts.

2. Description of Related Art

For many years solid phase chemistry has found a rapidly expanding utility in biopolymer synthesis and biopolymer immobilization. For example, organic and inorganic materials have been utilized for the solid phase synthesis of peptides and oligonucleotides by the step wise addition of activated amino acid derivatives or nucleotide derivatives to a growing oligomeric chain attached at one end to a solid support. Typically, the solid support material is in the form of a porous bead or resin material having a high surface area. Typically, in these solid phase systems, the chemically synthesized peptides or oligonucleotides are cleaved from the solid support and subsequently utilized in biochemical research or diagnostic applications. Thus, the solid support material plays no role in the research or diagnostic applications, having been used only during the initial synthesis of the biopolymer.

Additionally, solid phase chemistry has gained recognition for its usefulness in the study and the analysis of biopolymers. For example, cellulose membranes, polypropylene membranes, and nylon membranes have been widely used in blotting techniques which involve capturing native biopolymers onto the membrane and subsequently immobilizing the blotted biopolymer using heat, radiation or chemical techniques. The immobilized biopolymers are then available for subsequent analyses such as those associated with Southern blotting applications and reverse hybridization analytical techniques.

Additionally, presynthesized or natural oligonucleotides have been immobilized by covalently attaching activated oligonucleotides to the solid support. Typically, this approach requires activating the oligonucleotide with, e.g., a carbodiimide. Unfortunately, the activated oligonucleotides are expensive and they have short useful lives because they are very unstable. Thus, preparing and utilizing these activated oligonucleotides often lead to the loss of expensive reagents when the activated oligonucleotide decays to an inactive form. Moreover, carbodiimide activation frequently results in urea side product formation. Since these ureas tend to be insoluble in many common organic solvents their presence in automated reaction systems can cause problems when tubing and other lines are clogged by the precipitate.

More recently, oligonucleotides and peptides have been synthesized chemically to a solid support material directly and subsequently utilized without cleaving the biopolymers from the solid support. Generally, these support bound biopolymers are located at site specific locations on the solid support, with each site associated with at least one known biopolymer. Contacting, for example, site specifically bound oligonucleotides to unknown oligonucleotides under hybridizing conditions and subsequently determining the sites at which hybridization occurs can provide information relating to the structure and biological function of the unknown oligomer. Solid support materials suitable for such applications must physically and chemically withstand the temperatures and solvents associated with synthesizing the biopolymer onto the support, and not interfere with the hybridization and detection process.

Derivatized polypropylene films, glass slides and silicon wafers have been used for the solid support synthesis of oligonucleotides and peptides at site specific locations on the film, slide or wafer. These materials have been fairly successful because the glass, polypropylene and silicon withstand the physical and chemical rigors of the synthesis and hybridization processes. Furthermore, these materials are suitable when fluorescence detection techniques are used because they have low background fluorescence. However, glass slides, silicon wafers and polymer films are difficult to handle, and require handles or specially designed holders in order to manipulate the solid support when they are utilized in automated processes. These handles or holders are expensive to design and use and generally add to the costs of the utilizing solid supports. Furthermore, it is difficult to characterize and control the surface density of biopolymers synthesized or attached to glass slides and polypropylene films. Thus, there is a continuing need for improved materials suitable for immobilizing biopolymers and for materials suitable for directly synthesizing biopolymers. Such materials are preferably also suitable as solid supports for the evaluation of immobilized biopolymer biological activity, their identification or their use in analytical applications.

Accordingly, it is an object of the present invention to provide biopolymer immobilization reagents which are stable under conditions for synthesizing or immobilizing biopolymers and which are stable under conditions for the subsequent analysis of biopolymers.

It is also an object of the present invention to provide biopolymer immobilization reagents which are capable of being formed into devices which intrinsically incorporate holders or handlers.

It is a further object of the present invention to provide biopolymer immobilization reagents which are inexpensive and physically rugged.

It is another object of the present invention to provide biopolymer immobilization reagents whose compositions are controllable to provide greater or lesser surface densities of biopolymer synthesis.

It is another object of the present invention to provide reagents having surfaces suitable for immobilizing biopolymers at site specific locations and at high biopolymer densities.

It is also an object of the present invention to provide biopolymer immobilization reagents which utilize solid materials capable of forming films or flat planar surfaces and do not interfere with detection techniques.

It is further an object of the present invention to provide biopolymer immoblization reagents which have reasonable shelf lives and do not degrade at ambient conditions.

SUMMARY OF THE INVENTION

The present invention provides reagents for the immobilization of biopolymers and the subsequent use of immobilized biopolymers in analytical and diagnostic procedures. Advantageously, the reagents of the present invention are stable under biopolymer synthesis conditions and remain stable during analytical and diagnostic procedures. Moreover, materials suitable for preparing the reagents of the present invention are readily formed into objects having desired surface characteristics, e.g. planar surfaces, and having physical features to facilitate holding and handling during various processing steps. Additionally, the reagents of the present invention have extended shelf lives and do not require great caution for their storage.

More particularly, the present invention provides biopolymer immobilizing reagents which include a solid support fabricated of a polymeric material having at least one substantially planar, non-porous surface with pendant acyl fluoride functionalities. In preferred embodiments the polymeric material is ethylene-acrylic acid copolymer or ethylene methacrylic acid copolymer which has been activated to provide acyl fluoride functionalities on a flat surface. In another aspect the present invention includes processes for forming reagents which involve first providing suitable solid support material and activating at least one selected surface of the solid support material with reagent capable of forming acyl fluoride functionalities on the surface of the solid support, thus providing an activated solid support capable of immobilizing biopolymers by reaction with the active acyl fluoride functionalities. In preferred processes solid support material is a polymeric material fabricated of polymer having pendant carboxyl functionalities.

Additional processes contemplated as being within the scope of the present invention include those which utilize solid supports fabricated of ethylene acrylic acid copolymer or ethylene methacrylic acid copolymer. In accordance with the present invention such processes include activating a surface of the solid support with a composition capable of forming an active acyl group, thus providing an activated solid support capable of immobilizing biopolymer or biomonomer by reacting biopolymer or biomonomer with the activated solid support to immobilize the biopolymer or biomonomer.

In another aspect, the present invention provides processes for preparing an immobilized biopolymer which include first providing a solid support fabricated of a polymeric material and having at least one surface incorporating pendant acyl fluoride functionalities. Then contacting the surface with derivatized biopolymer or biomonomer under appropriate reaction conditions results in the attachment of the derivatized biopolymer or biomonomer to the solid support surface. Typically, when the solid surface is utilized to immobilize biomonomer the process further includes successively reacting biomonomer units to form a growing biopolymer which is attached or immobilized to the solid support surface. In preferred embodiments the solid support is fabricated of ethylene acrylic acid copolymer or ethylene methacrylic acid copolymer which has been derivatized to form pendant fluoride functionalities.

In another embodiment of the present invention processes for preparing an immobilized biopolymer or biomonomer are provided which include attaching derivatized biopolymer or biomonomer to a solid support fabricated of ethylene acrylic acid copolymer or ethylene methacrylic acid copolymer. This aspect of the invention involves the direct attachment of biopolymer or biomonomer by reacting pendant carboxylate functionalities of the copolymer with derivatized biopolymer or biomonomer.

Advantageously the many aspects of the present invention provide reagents and biopolymer immobilization processes which overcome disadvantages associated with prior art reagents and methods. Those skilled in the art will appreciate that the reagents of the present invention provide physically and chemically stable supports capable of immobilizing biopolymers at site specific locations on a planar surface. Moreover, reagents and processes of the present invention are capable of providing immobilized biopolymer present on the surface of a solid support at higher than expected densities. As a feature, the polymeric materials forming the reagents described herein may be adjusted to provide greater or lesser densities of biopolymer attachments as required and are capable of being formed into objects incorporating useful mechanical features such as holders or handlers.

These and other advantages associated with the present invention will become apparent to those skilled in the art upon an understanding of the invention as described in the detailed description of the invention taken in combination with the following drawings.

DETAILED DESCRIPTION OF THE INVENTION

Figure 1:
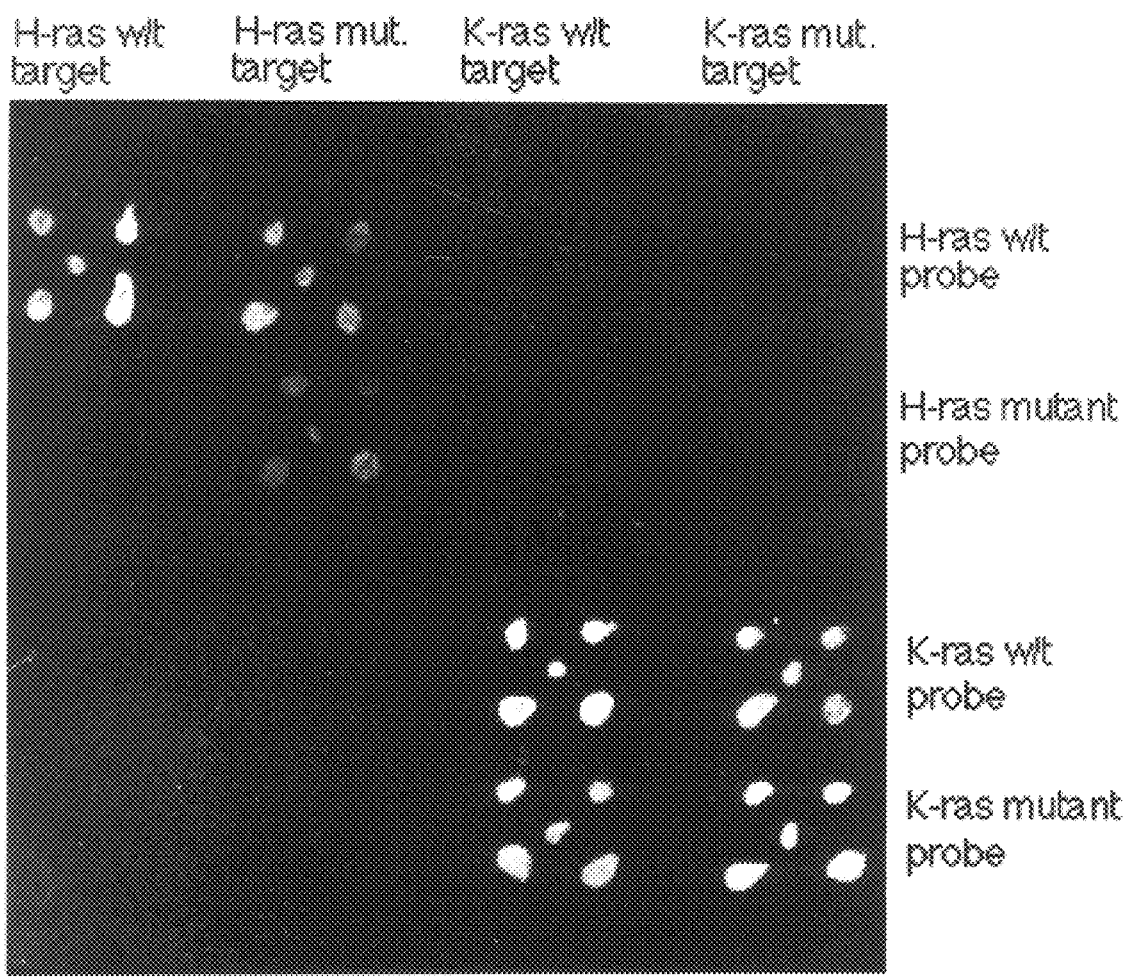
FIG. 1 shows CCD camera results obtained from the reverse hybridization of complementary H-ras and K-ras oligonucleotides utilizing oligonucleotides immobilized onto acyl fluoride activated polypropylene film in accordance with the present invention.

The present invention provides immobilization reagents, methods for their preparation, and methods for their use in preparing immobilized biopolymers. The reagents and methods of the present invention are particularly suitable in the preparation and use of biopolymer arrays for evaluating biological activity, determining the presence or absence of selected sequences of nucleic acids, and sequencing DNA. For example, designed DNA libraries consisting of site-specific arrays of oligonucleotides of known sequence immobilized to a solid support surface have utility in detecting individual genetic mutations using reverse hybridization techniques. Those skilled in the art will recognize that the present invention has additional utility in the area of DNA and peptide synthesis in general. In particular, the reagents of the present invention are solid supports suitable for the solid support synthesis of biopolymers or the attachment of biopolymers. As such their utility broadly applies to the general field of immobilized biopolymers.

More particularly, a first aspect of the present invention includes reagents for immobilizing a biopolymer, the reagent including a solid support fabricated of a polymeric material having at least one surface with pendant acyl fluoride functionalities. Because the reagents of the present invention are particularly useful in the preparation of biopolymer arrays for the evaluation or identification of biological activity, the solid support is preferably in the form of a device having at least one flat planar surface. The size of the solid support can vary and depends upon the final use of the immobilized biopolymer. Those skilled in the art will appreciate that arrays of biopolymers immobilized on miniaturized solid supports have been under development for many years. These solid supports can be measured in terms of $mm^2$ and can have numerous different immobilized biopolymers with each different biopolymer attached to a different site specific location on the miniaturized solid support. Solid supports in the form of dip sticks are also within the scope of the present invention. As known in the art dip sticks typically are rectangular in shape with each side measuring a few centimeters. On the other hand, large biopolymer arrays such as oligonucleotide arrays utilized for sequencing whole genomes may have dimensions measuring a meter or more.

In order to accommodate a number of different synthetic and testing techniques including specialized automated synthesis and testing equipment, suitable solid supports can also be molded into any of a variety of shapes. For example, it may be advantageous to mold a biopolymer array holder of the same polymeric material utilized to fabricate the solid support. In such a system the holder is the solid support and may be any shape including one which is easily handled by an automated diagnostic system in which robotic arms move biopolymer arrays between reaction stations and detection stations. Preferably, when such a holder is the solid support, it incorporates a planar or continuous surface suitable for attaching biopolymers.

In accordance with one aspect of the present invention, polymeric materials suitable for fabricating solid supports can be any material capable of being derivatized to form acyl fluoride functionalities on at least one surface of the solid support. For example, polymeric materials with pendant carboxyl functionalities or polymeric materials capable of being modified to support carboxyl groups can be reacted with suitable reagents to form acyl fluoride functionalities. In preferred embodiments, reagents of the present invention utilize solid supports fabricated of ethylene acrylic acid copolymers, ethylene methacrylic acid copolymers, or derivatized polypropylene. Advantageously, ethylene acrylic acid copolymers and ethylene methacrylic acid copolymers can be thermally molded into a variety of shapes and are excellent film formers. For example, thermoset ethylene acrylic acid and ethylene methacrylic acid copolymers can be used to mold and thermally set a molded solid support. Alternatively and preferably, thermoplastic noncrosslinked ethylene acrylic acid and ethylene methacrylic acid copolymers are utilized to extrude a film or mold a part into a desired configuration. Accordingly, these copolymeric materials are sufficiently versatile for a variety of applications including those in which the solid support is in the form of a film and those applications in which the physical form of the solid support takes on a three dimensional functional shape. Additionally, ethylene acrylic acid copolymer and ethylene methacrylic acid copolymers do not nonspecifically absorb biopolymers. This is an important consideration because diagnostic applications which depend upon detecting reagents specifically bound to biopolymers immobilized to solid supports cannot tolerate nonspecific binding to the solid support. Other favorable characteristics of ethylene acrylic acid copolymers and ethylene methacrylic acid copolymers include their non-porous nature and their chemical and physical stability in solvents and reagents typically used in the synthesis and analysis of biopolymers. An important consideration and advantage of polymeric materials in which the carboxyl functionality is incorporated in the polymeric structure is the high density of the pendant carboxyl functionality and its statistically even distribution throughout the polymer. Ethylene acrylic acid and methacrylic acid copolymers can be chosen for their ratio of ethylene to acid, therefore providing a means for controlling the density of active sites for immobilizing biopolymers.

Those skilled in the art will recognize that polymeric materials capable of being derivatized to support carboxyl groups which in turn can be modified to provide surface acid fluoride functionalities include a wide range of materials. For example, aminated polypropylene reacted with a cyclic anhydride, e.g. succinic anhydride, to provide carboxyl groups suitable for converting to acyl fluoride is particularly useful. Another suitable polymeric material includes polyvinyl alcohol derivatized with, for example, an alkyl diacid to form a pendant carboxyl group:

Polyvinyl alcohol

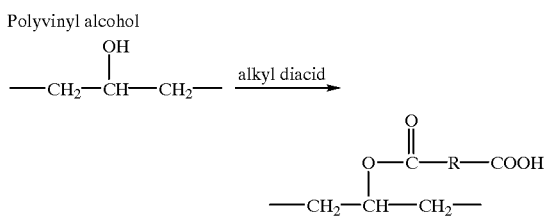

Additional suitable polymeric materials include methyl-methacrylate or methylacrylate saponified to expose a pendant carboxyl group:

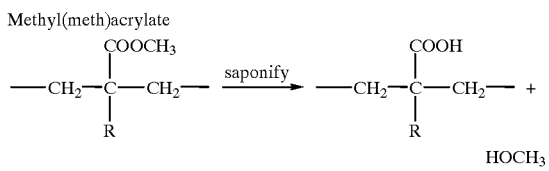

Still other polymeric materials easily derivatized to provide a reactive carboxyl group are hydrolyzed polyacrylonitrile or hydrolyzed polymethacrylonitrile:

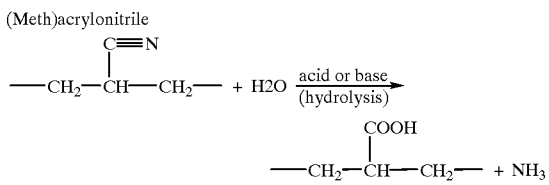

In accordance with the present invention suitable reagents for forming acyl fluoride functionalities on at least one surface of the solid support broadly include carboxyl reactive fluoridating reagents. A most preferred reagent is (diethylaminosulphur)trifluoride (DAST) which reacts with pendant carboxyl groups in the following reaction:

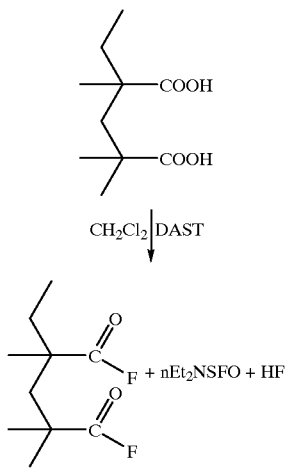

Other reagents include cyanuric fluoride:

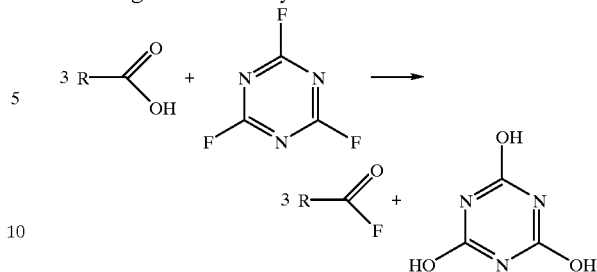

and tetramethylfluoroformadinium hexafluorophosphate:

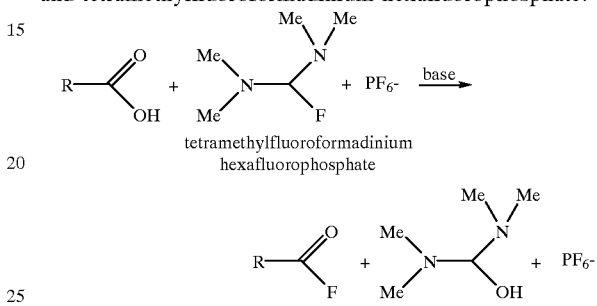

In a most preferred embodiment of the present invention, ethylene acrylic acid copolymers or ethylene methacrylic acid copolymers formed into sheets having a thickness of about 0.5 mm are modified on at least one surface by exposing the surface to about a 5% solution of DAST for a period of several hours. After stopping the reaction using dichloromethane and acetonitrile washes the film is ready for use in immobilizing or synthesizing biopolymers as described below. Advantageously, it has been discovered that acyl fluoride activate polymeric materials are surprisingly stable at ambient conditions and when stored in a cool dry environment have unlimited shelf lives.

In another aspect, the present invention provides methods for preparing reagents for immobilizing biopolymers which include providing a solid support fabricated of ethylene acrylic acid copolymer or ethylene methacrylic acid copolymer and derivatizing at least one surface of the solid support by reacting the surface with an activating agent. Suitable activating agents are reagents capable of reacting with the acrylic or methacrylic carboxyl group to form reactive pendant functional groups, e.g. active acyl functionalities. As will be discussed below, preferably the active pendant functional groups will react readily with biopolymer or biomonomer derivatized with at least one amino functionality to form amide groups. For example, activating agent $PCl_5$ (phosphorous pentachloride) will convert carboxyl groups to an acid chloride; carbodiimides will convert carboxyl groups to an isourea; anhydrides can be prepared by reacting with suitable carboxylated leaving groups and an activating agent; hydrazides will convert carboxyl groups to azides. Additionally, active esters can be formed on the surface utilizing suitable alcohols and an activating agent. Other suitable reagents include phosphonium reagents and N-carboxyanhydrides.

The reagents of the present invention have particular utility in processes for immobilizing biopolymers for subsequent use in evaluating biological activity, diagnosing disease states, or determining monomeric sequences of the biopolymer samples. Accordingly, the present invention further provides processes for immobilizing biopolymers which, in one aspect, involve first providing a solid support fabricated of a polymeric material having at least one surface with pendant acyl fluoride functionalities; and then contacting the surface with a suitably derivatized biopolymer or derivatized biomonomer under conditions which cause the derivatized biomonomer or biopolymer to react with acyl fluoride functionalities. Preferred polymeric materials are acyl fluoride activated ethylene acrylic acid copolymers, acyl fluoride activated ethylene methacrylic acid copolymers, or acyl fluoride activated derivatives of polypropylene. However, those skilled in the art will recognize that any acyl fluoride activated polymeric material having physical and chemical properties appropriate for preparing and using the immobilized biopolymers is suitable.

In preferred processes, the derivatized biopolymers are amino derivatized biopolymers, e.g. amino derivatized oligonucleotides and peptides having the following general structures:

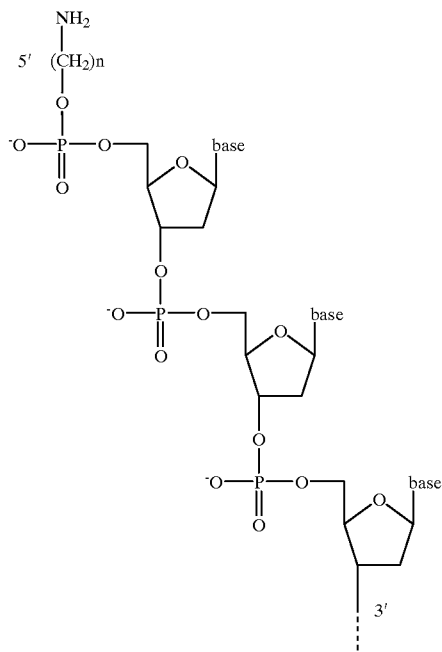

The amino derivatized oligonucleotide shown is derivatized at its 5' end phosphate. However, those skilled in the art will appreciate that any number of sites on the oligonucleotide can be selected to attach the amino group, including the base sites on the sugar moieties. Amino derivatized biopolymers are preferred because amide linkages resulting from the reaction of acyl fluoride functionalities with the amino functionalities are stable and the reaction kinetics associated with the amide bond formation is favorable. However, it is also within the scope of this aspect of the present invention to provide processes for immobilizing biopolymers which involve contacting suitably derivatized biopolymers with the acyl fluorides under conditions which result in ester bond formations. Biopolymers suitable in the practice of this embodiment include alkyl hydroxy or hydroxy derivatized oligonucleotides and peptides. Those skilled in the art will recognize that reaction conditions can be tailored so that a nucleotide phosphate hydroxyl reacts with acyl fluorides to immobilize an oligonucleotide.

The step of contacting the acyl fluoride activated surface of the solid support under conditions which cause amino derivatized biopolymer to react with the acyl fluoride is accomplished by exposing the solid support surface to derivatized biopolymer in the presence of an aqueous base. Bringing the acyl fluoride functionalities into contact with the amino biopolymer results in the displacement of the fluoride and the formation of an amide bond. The reaction between the acyl fluoride and amino derivatized biopolymer is rapid at room temperatures and will typically will go to completion in a matter of seconds. The immobilized biopolymer has a shelf life exceeding six months.

The following shows a generalized reaction between an amino derivatized oligonucleotide and a solid support surface activated with acyl fluoride functionalities:

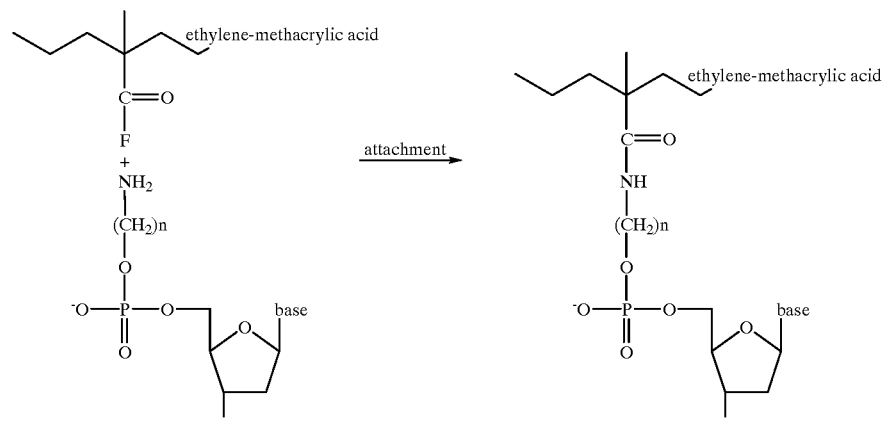

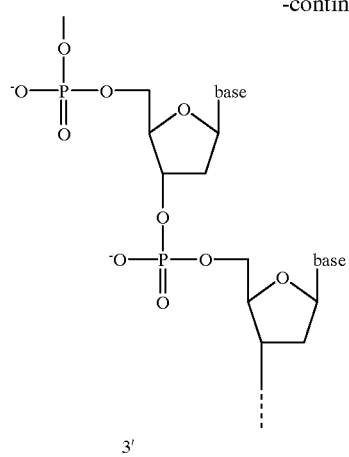

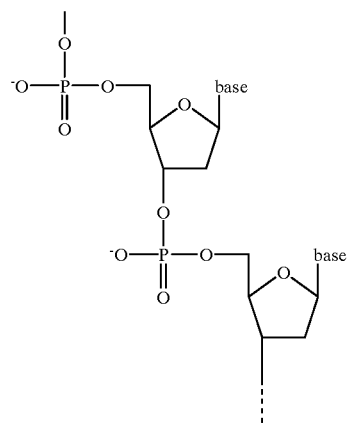

The amino derivatized oligonucleotides are prepared by attaching a primary aliphatic amine to the 5' terminus of an oligonucleotide. Reagents and instructions for their use in attaching primary aliphatic amine to oligonucleotides are commercially available from Clontech Laboratories, Inc. of Palo Alto, Calif. (See Clontech Product Protocol, PR71095 "N-MMT-$C_n$-AminoModifiers".)

Similarly any protein or peptide with surface amino groups, e.g. lysine can be immobilized to a solid support having pendant acyl fluoride functionalities:

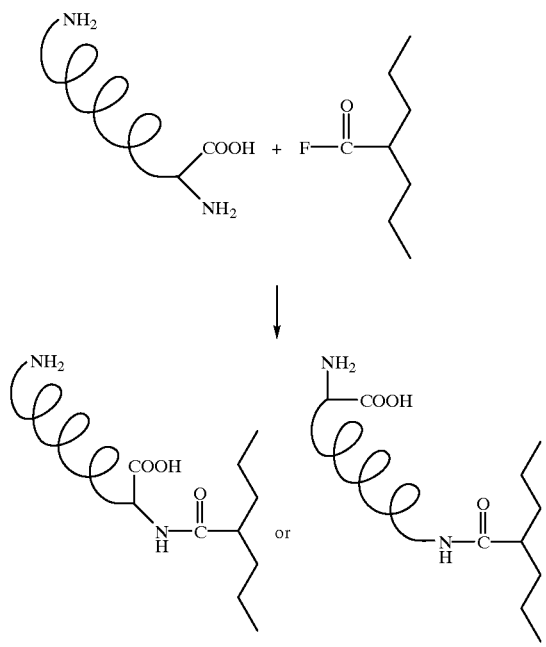

In accordance with the present invention, it is preferable, subsequent to forming the amide linkages and immobilizing the biopolymer, to "block" the nonreacted acyl fluoride functionalities from further unwanted reactions. In the generalized reaction shown above the unreacted acyl fluoride functionalities are reacted during the final wash stage with an ammonium hydroxide system to form amide blocking functionalities. Those skilled in the art will recognize however, that a host of blocking reactions are possible. For example, blocking esters are formed by reacting the acyl fluoride with a secondary and primary alcohol. Similarly, in addition to ammonium hydroxide, primary or secondary amines can be used to form amide blocking functionalities.

As mentioned above, many applications for utilizing immobilized biopolymers require that biopolymers be immobilized at site specific locations on a solid support surface. In order to prepare ordered arrays of biopolymers, including grids and 1×n arrays of immobilized biopolymer, each biopolymer located at site specific locations, a preselected site on the surface of the activated polymeric material is exposed to a solution of the desired amino derivatized biopolymer. In accordance with the present invention, this can be accomplished manually by applying on the order of 2 μL of derivatized biopolymer solution to a preselected location on the polymeric material. Alternatively, thermal inkjet printing techniques utilizing commercially available jet printers and piezoelectric microjet printing techniques as described in U.S. Pat. No. 4,877,745 can be utilized to spot selected solid support surface sites with selected derivatized biopolymers.

While the reagents of the present invention are particularly useful for immobilizing presynthesized or available oligonucleotides, proteins and peptides, they are also suitable for the direct solid support synthesis of oligonucleotides and peptides. Thus, the present invention additionally provides processes for attaching a biomonomer unit to a solid support fabricated of a suitable polymeric material and the subsequent stepwise successive addition of biomonomer units to a growing biopolymer chain. In accordance with this aspect, preferred embodiments involve directly synthesizing oligonucleotides or peptides to ethylene acrylic acid copolymers or ethylene methacrylic acid copolymers which have been derivatized to provide a "linker" compound attached via an amide moiety to the copolymer. Advantageously, the amide moiety is stable to the chemistries used during the synthesis procedures and can be formed by directly reacting an amine with the carboxyl functionality of the copolymer. Alternatively, the process can involve forming an amide linked "linker" compound by reacting an amine with an acyl halide functionality formed on the surface. The acyl halide can be acyl fluoride prepared as described above or any other acyl halide prepared utilizing methods known in the art.

The following illustrates as exemplary synthetic pathway for the direct synthesis of oligonucleotides.

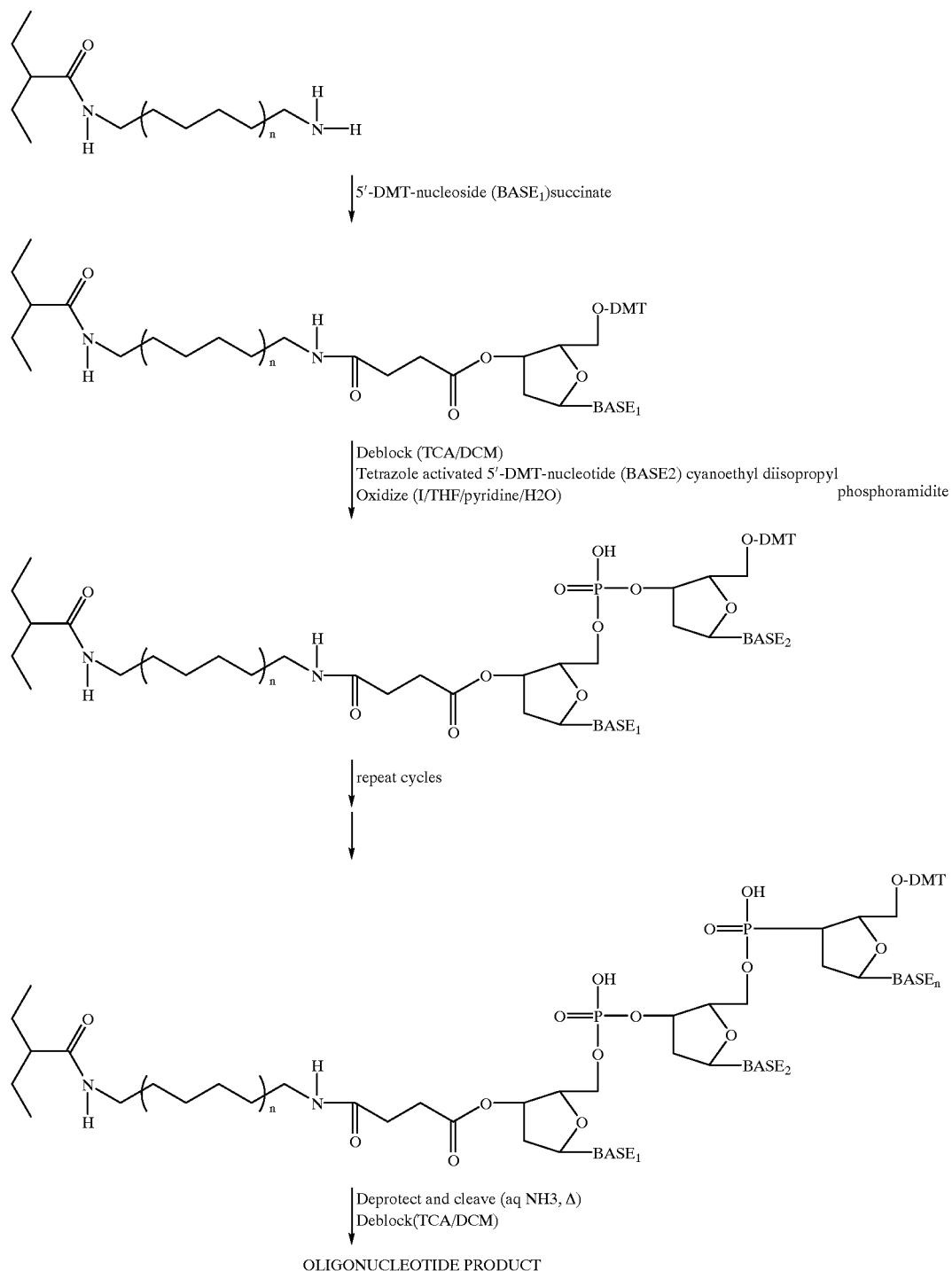

Although preferred oligonucleotide synthesis methods are those based upon phosphoramidite chemistries, those skilled in the art will recognize that other methods are equally applicable. Alternative methods include the phosphite-triester method which utilizes deoxyribonucleoside-3'-phosphomonochloridites or deoxyribonucleoside-3'-phosphomonotetrazolides in a stepwise synthesis(Matteucci, M. D., et al. *Journal of the American Chemical Society,* 103:3185, 1981.); the phosphotriester method (Sproat, B. S. & Gait, M. J. "Oligonucleotide Synthesis, a Practical Approach: IRL Press, p. 83, 1984); and, the H-phosphonate method (Froehler, B. C. & Matteucci, J. D. *Tetrahedron Letters,* 27:469 1986)

In another aspect, the present invention includes methods for the direct synthesis of peptides to ethylene acrylic acid copolymers, ethylene methacrylic acid copolymers, and acyl fluoride activated polymers. The following details a representative scheme for the step-wise direct synthesis by the successive addition of activated amino acids to provide peptide immobilized to a solid support.

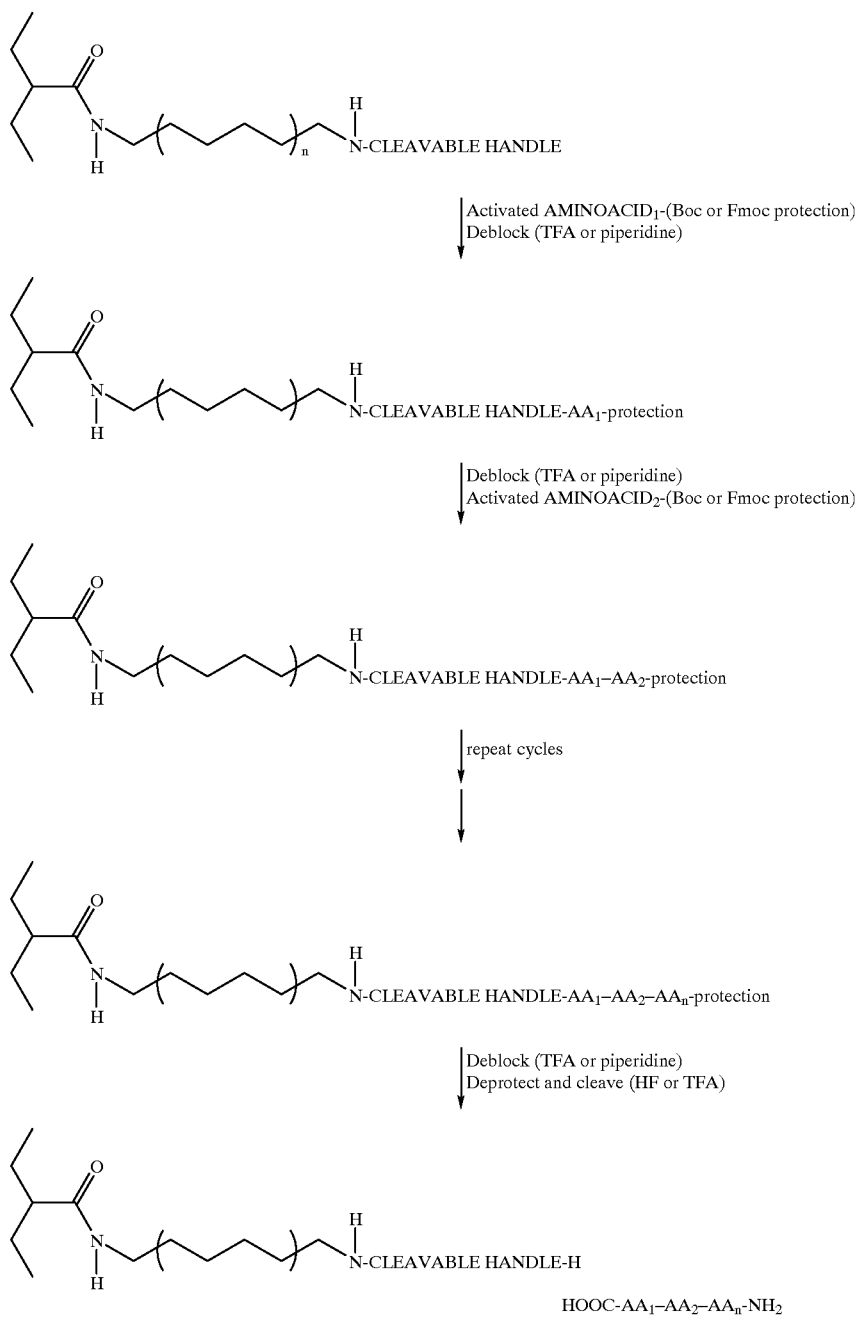

As mentioned above, the utility of biopolymers immobilized in accordance with the present invention includes utilizing arrays of biopolymers immobilized at site specific locations on a planar solid support surface. In embodiments in which the biopolymers are directly synthesized to the solid support surface the synthesis is performed in an ordered manner so that the biopolymers are immobilized at specific solid support locations. Devices and automated instrumentation for obtaining arrays of immobilized biopolymers are known in the art. For example, U.S. Pat. No. 5,429,807 describes array maker apparatus and methods for obtaining ordered arrays of immobilized oligonucleotides using direct synthesis procedures.

Having now generally described the invention, the same will be more readily understood through reference to the following examples which are provided by way of illustration, and are not intended to be limiting of the present invention, unless so specified.

EXAMPLE 1

The following describes a method for preparing a reagent for immobilizing biopolymers in accordance with the present invention. More particularly, the following example describes a method for preparing an acyl fluoride activated solid support by aminating and derivatizing polypropylene film.

Polypropylene film (purchased from Mobil) having a thickness of approximately 0.03 mm was aminated by exposing the film surface to a radio frequency plasma in the presence of ammonia following the procedures described in U.S. Pat. No. 5,112,736. The aminated film was then washed with acetonitrile and then derivatized to form carboxyl functionalities linked to its surface by contacting the aminated surface with an aqueous solution of 0.1 M $NaHCO_3$ and 0.1 M succinic anhydride in a closed container for about 16 hours. The film was removed from the aqueous solution and washed once with methanol followed by three washes with isopropyl alcohol and air drying.

In order to "block" the aminated sites which did not react with the succinic anhydride the carboxylated film was then brought into contact with an acetic anhydride solution containing about 0.25% dimethylaminopyridine. Following the residual amino group conversion to acetamide functionalities the film was washed three times with isopropyl alcohol and then air dried.

The carboxyl linked and amine blocked polypropylene film was then placed in a sealed container containing a 5 vol % solution of (diethylamino)sulfur trifluoride (DAST) in methylene chloride and shaken for about 16 hours. After removing the solid support from the reaction container it was washed with dichloromethane followed by an acetonitrile wash and air drying. This acyl fluoride derivatized film was stable during a six month storage under cool and dry conditions.

The just described procedure can be graphically described by the following reaction scheme:

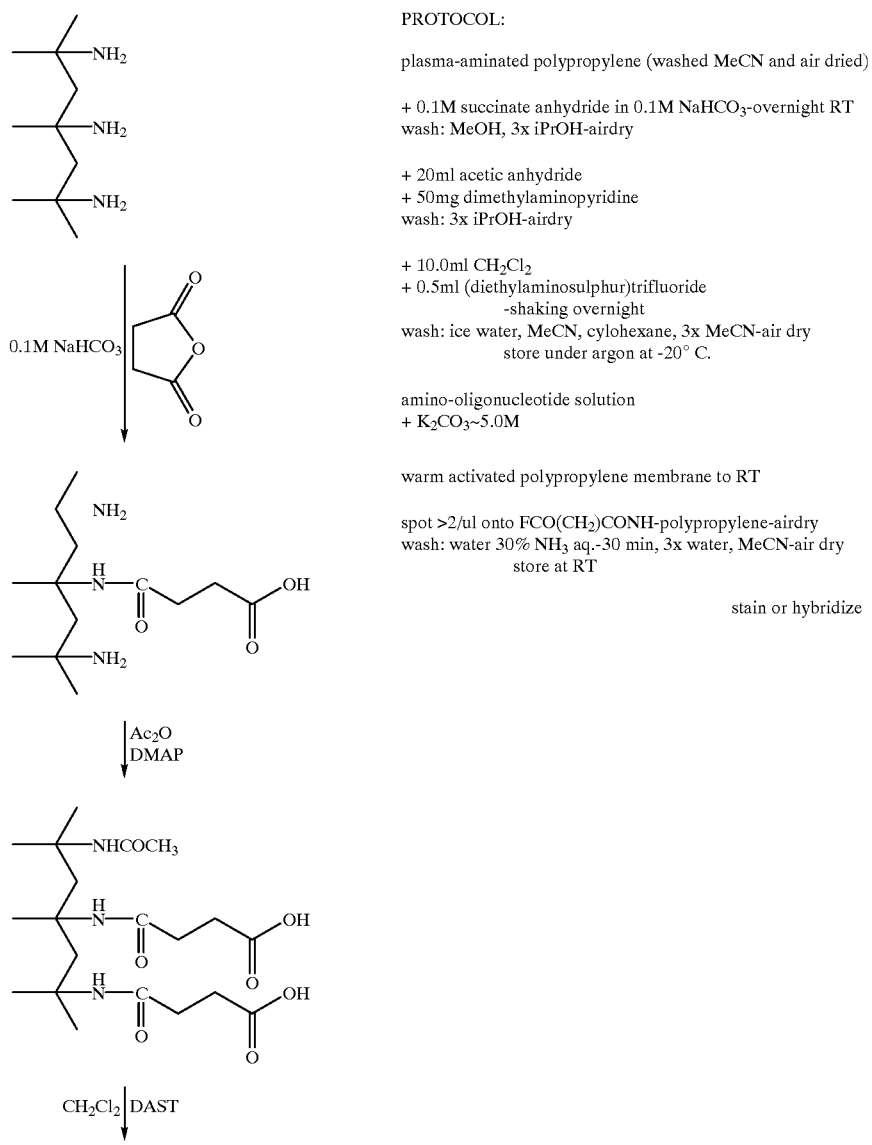

PROTOCOL:

plasma-aminated polypropylene (washed MeCN and air dried)

+ 0.1M succinate anhydride in 0.1M $NaHCO_3$-overnight RT
wash: MeOH, 3x iPrOH-airdry + 20ml acetic anhydride
+ 50mg dimethylaminopyridine
wash: 3x iPrOH-airdry + 10.0ml $CH_2Cl_2$
+ 0.5ml (diethylaminosulphur)trifluoride
 -shaking overnight
wash: ice water, MeCN, cylohexane, 3x MeCN-air dry
 store under argon at -20° C.

amino-oligonucleotide solution
+ $K_2CO_3$~5.0M warm activated polypropylene membrane to RT spot >2/ul onto $FCO(CH_2)CONH$-polypropylene-airdry
wash: water 30% $NH_3$ aq.-30 min, 3x water, MeCN-air dry
 store at RT stain or hybridize -continued

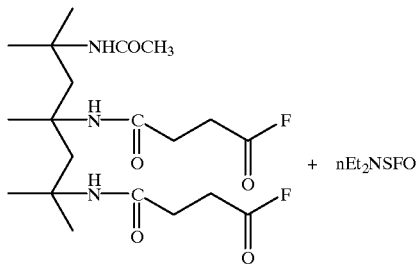

EXAMPLE 2

The following describes a method for preparing a reagent for immobilizing biopolymers in accordance with the present invention. More particularly, the following example describes a method for preparing an acyl fluoride activated solid support by derivatizing ethylene acrylic acid copolymer and ethylene methacrylic acid copolymer strips and film.

Ethylene acrylic acid copolymer, available from Dow Chemical Co. under the tradename Primacor, and ethylene methacrylic acid copolymer, available from DuPont under the tradename Nucrel, were injection molded into strips about 0.5 mm thick. Selected Nucrel strips were impregnated with carbon black during the molding process. Ethylene methacrylic acid copolymer film about 0.05 mm thick was obtained from DuPont. The molded strip and film was washed with acetonitrile and allowed to air dry. The dried strips and film were placed in a closed container containing a 5% v/v solution of (diethylaminosulphur)trifluoride in methylene chloride and shaken for about 16 hours. These acyl fluoride activated molded strips were then removed from the methylene chloride solution, successively washed with methylene chloride and acetonitrile and three times with acetonitrile and then air dried.

The just described procedure can be graphically described by the following reaction scheme:

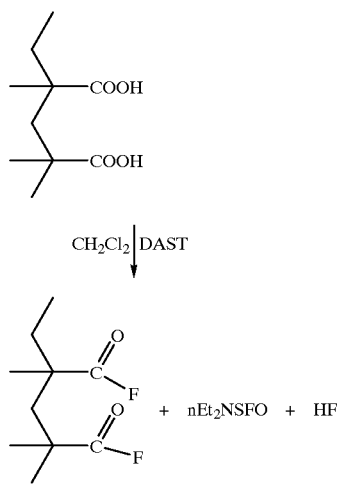

EXAMPLE 3

The following describes a method of immobilizing amino derivatized oligonucleotides to a solid support in the form of a film fabricated of acyl fluoride activated polypropylene and strips fabricated of acyl fluoride activated ethylene acrylic acid copolymer and ethylene methacrylic acid copolymer.

Short wild type and mutant oligonucleotide sequences were purchased from Genosys Biotechnologies, Inc. and their 5' terminus was amino derivatized with N-MMT-C12 AminoModifier cyanoethylphosphoramidites from Clontech Laboratories according to the manufacturer's directions. Oligonucleotide sequences complementary to the H-ras and K-ras wild type and mutant sequences were purchased and biotinylated at their 5' ends utilizing the Clontech Biotin-ON™ Phosphoramidite Product Protocol #PR71093. Similarly, 5'-amino $T_{1\,8}$ and 5'-biotinylated $A_{1\,8}$ oligonucleotides were obtained form the same sources for use as non-specific control sequences.

The acyl fluoride activated polypropylene film as prepared in example 1 and the acyl fluoride activated strips of ethylene acrylic acid copolymer, ethylene methacrylic acid copolymer and ethylene methacrylic acid copolymer impregnated with carbon black during the molding process, and the ethylene methacrylic acid copolymer film prepared in Example 2, were warmed to room temperature after storage at $-20°$ C. Approximately $2 \times 10^{-4}$ M solutions of each of the above described H-ras and K-ras amino derivatized oligonucleotides were prepared in an aqueous solution of 5M $K_2CO_3$. Spots of each solution were applied in a square pattern to the strips and film using between 0.5 μL and 2.0 μL of each solution. After the spots dried under ambient conditions the strips and film were washed with water followed by three washes with a 30% aqueous ammonia solution for 30 minutes each. The aqueous ammonia wash served to block acyl fluoride functionalities on the surface of the ethylene acrylic acid and ethylene methacrylic acid copolymers which were not utilized in the reaction between the acyl fluorides and the amino derivatized oligonucleotides. After a final wash with acetonitrile the strips and film containing immobilized H-ras and K-ras oligonucleotides were allowed to dry and then stored at room temperature. In order to provide nonspecific controls for evaluating the immobilized oligonucleotides the 5'-amino $T_{18}$-3' probe was applied to selected strips of acyl fluoride activated solid supports under the same conditions.

Utilizing the Invitrogen DNA DipStick qualitative colorimetric staining technique it was determined that all oligonucleotides showed roughly equivalent attachment of the amino derivatized probes.

EXAMPLE 4

The following describes processes for utilizing the immobilized oligonucleotides prepared in Example 3.

Each of the biotinylated oligonucleotides described in Example 3 were diluted in 2×SSPE buffer and each strip and film was incubated at room temperature with a different biotinylated oligonucleotide solution. Additionally, a few strips were incubated with a the 5'-biotinylated $A_{1\,8}$. The strips were removed from the solutions and then incubated with a 2×SSPE buffer solution of a streptavidin Cy-5 dye complex purchased from Amersham. Cy-5 is a cyanine dye having a fluorescent emission in the near infra red. Immobilized oligonucleotide probes which have hybridized with their complementary biotin labeled target will emit a fluorescent signal when excited with the appropriate wavelength.

Figure 2:
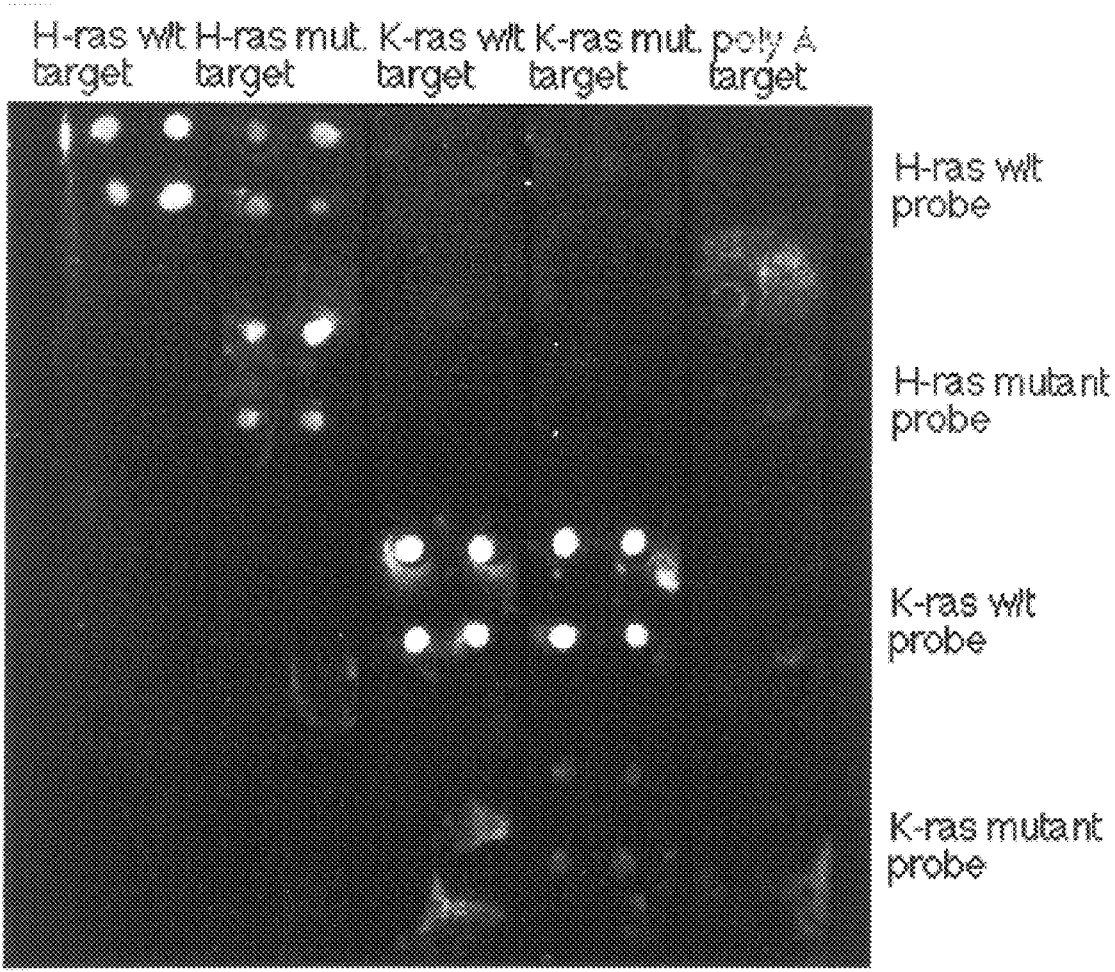
FIG. 2 shows CCD camera results obtained from the reverse hybridization of complementary H-ras and K-ras oligonucleotides utilizing oligonucleotides immobilized onto acyl fluoride ethylene methacrylic acid film.
Figure 3:
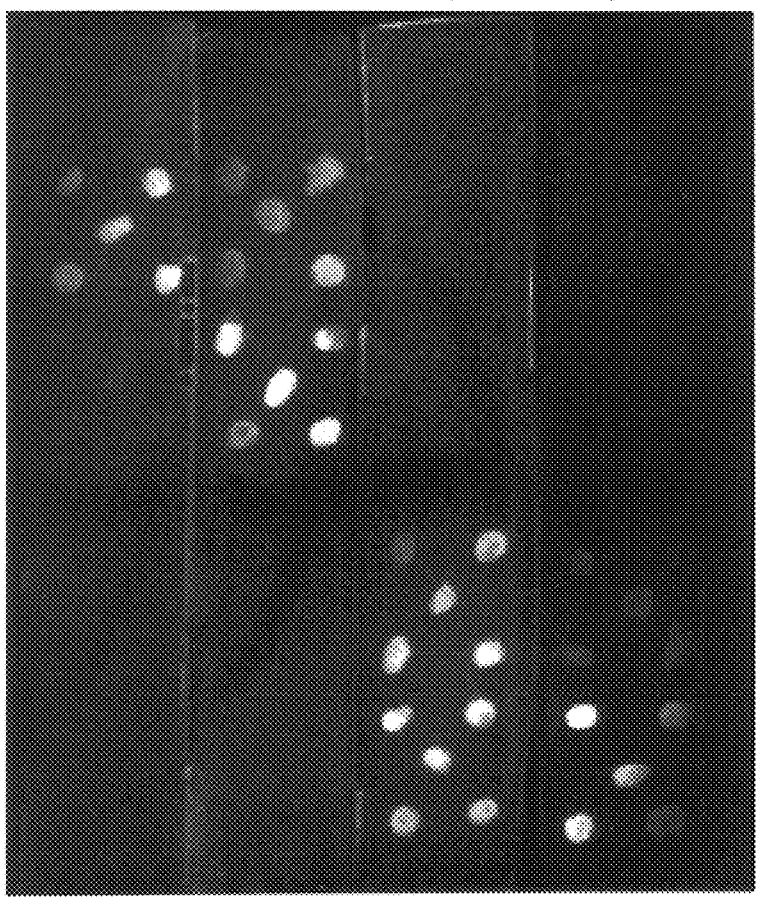
FIG. 3 shows CCD camera results obtained from the reverse hybridization of complementary H-ras and K-ras oligonucleotides utilizing oligonucleotides immobilized onto acyl fluoride activated ethylene acrylic acid molded strips.
Figure 4:
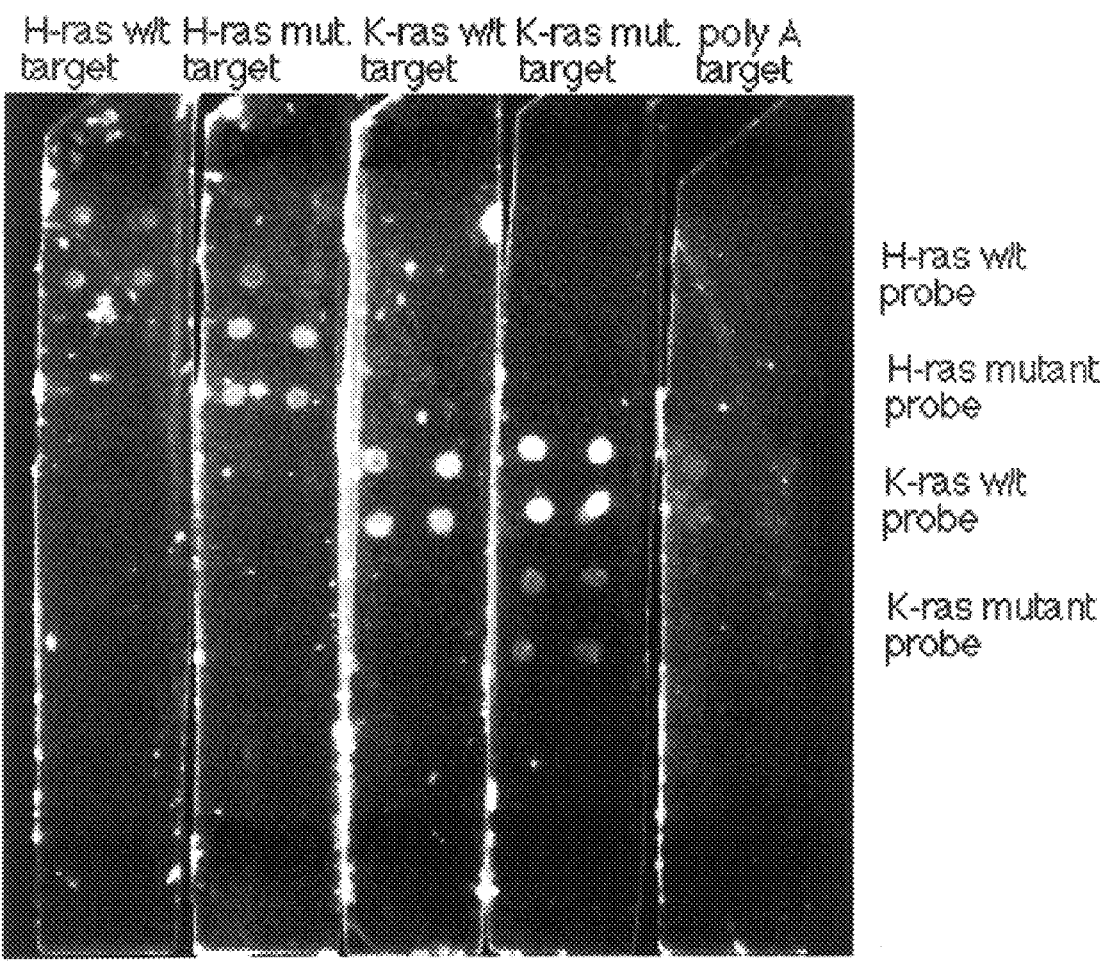
FIG. 4 shows CCD camera results obtained from the reverse hybridization of complementary H-ras and K-ras oligonucleotides utilizing oligonucleotides immobilized onto acyl fluoride activated ethylene methacrylic acid molded strips.
Figure 5:
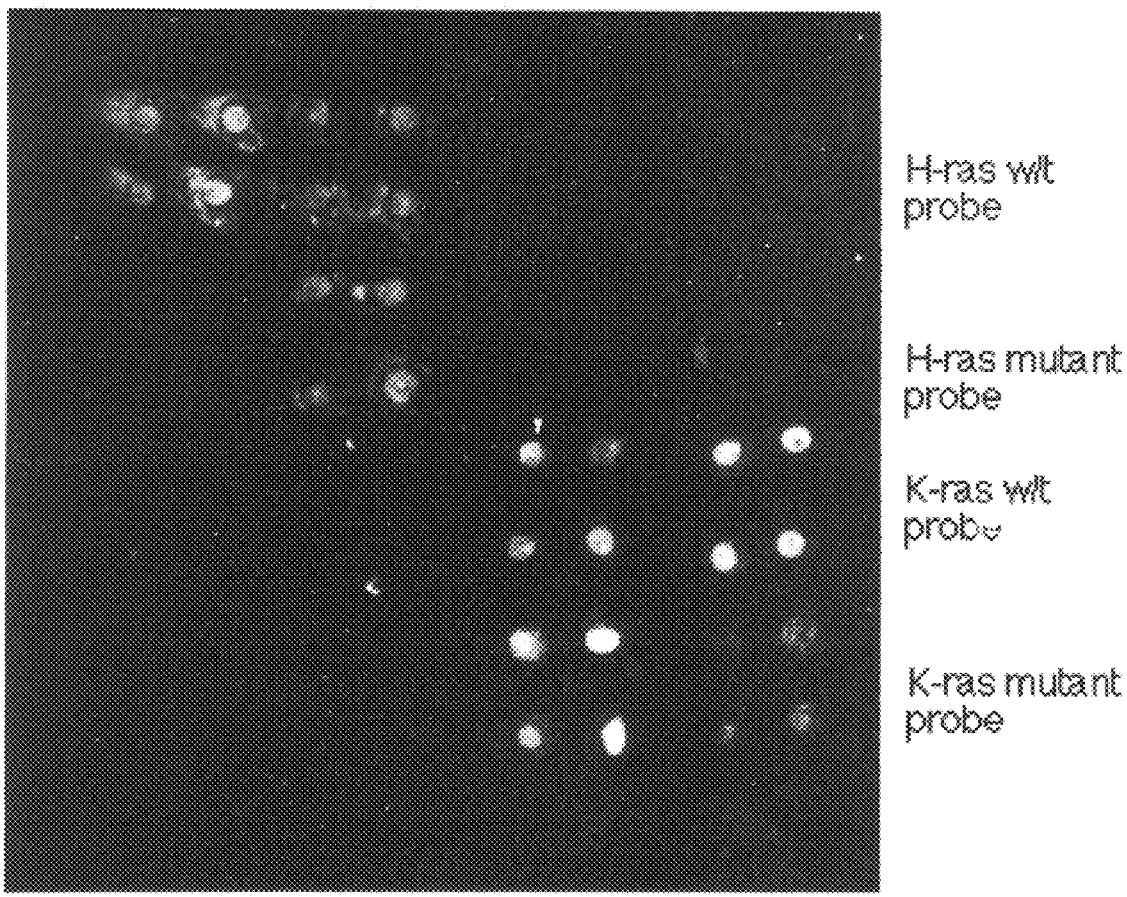
FIG. 5 shows CCD camera results obtained from the reverse hybridization of complementary H-ras and K-ras oligonucleotides utilizing oligonucleotides immobilized onto acyl fluoride activated ethylene methacrylic acid molded substrate impregnated with carbon black.
Figure 18:
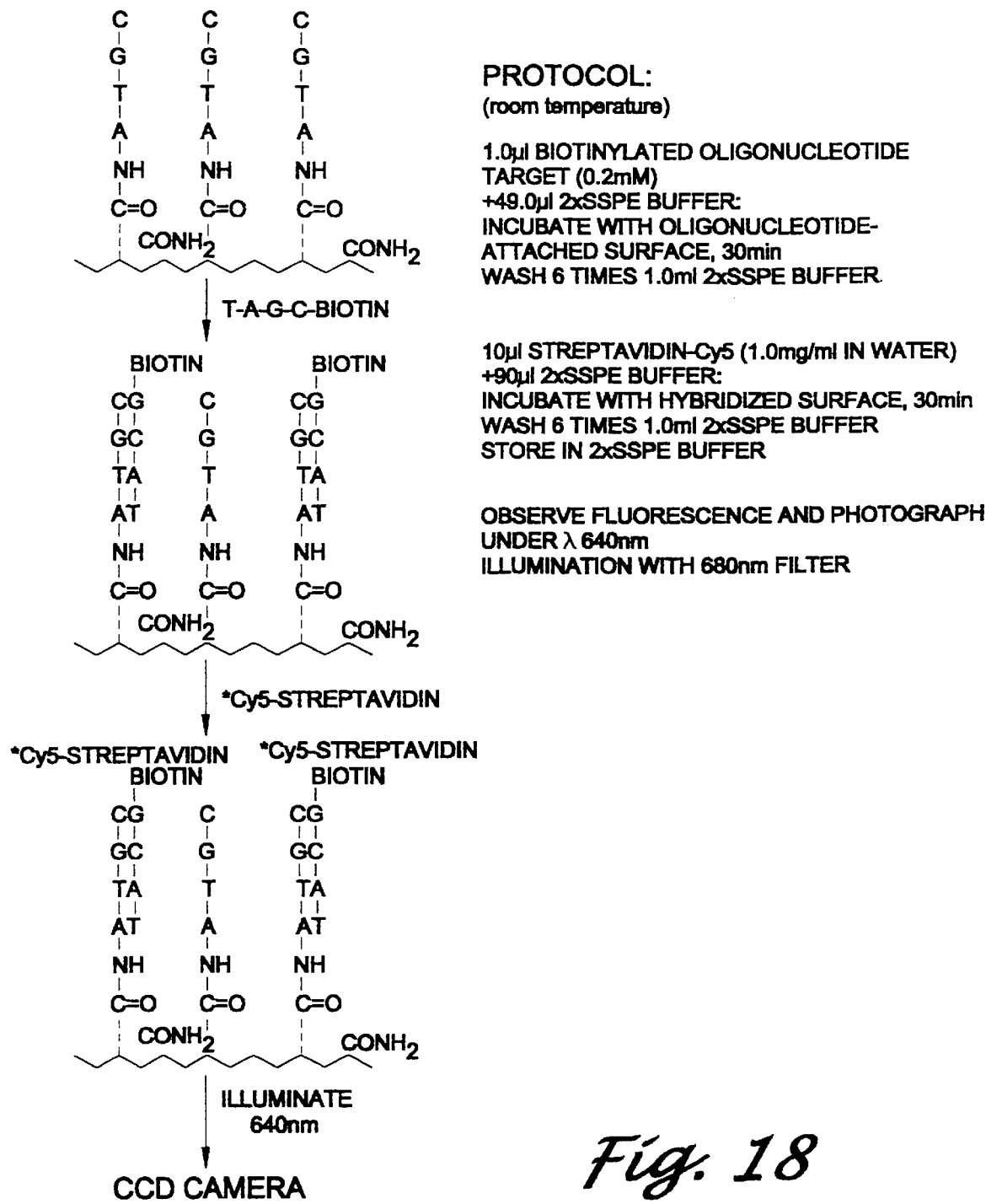
FIG. 18 is a flow chart indicating the general fluorescence detection technique utilized to detection hybridized oligonucleotides as shown in FIGS. 1–7.

The strips and film were illuminate by incandescent light with a 640 mm bandpass filter and photographed with a CCD (charge-coupled device) camera through a 680 nm bandpass filter. FIG. 18 shows a flow diagram of the hybridization and fluorescent detection techniques utilized in this experiment. FIGS. 1–5 illustrate the results obtained from the CCD camera exposure. The fluorescent emission is indicated by light colored spots on the solid support. FIG. 1 shows the results obtained with the acyl fluoride activated polypropylene film substrate. FIG. 2 illustrates the results obtained from acyl fluoride activated ethylene methacrylic acid film. FIG. 3 demonstrates the results obtained from the acyl fluoride activated ethylene acrylic acid molded strips. FIG. 4 shows the results from an ethylene methacrylic acid molded substrate. FIG. 5 demonstrates results obtained when the ethylene methacrylic acid molded substrate was impregnated with carbon black during the molding process.

The results of the just described reverse hybridization process as shown in FIGS. 1–5 demonstrate that no cross-hybridization between H-ras, K-ras, and Poly-A occurred. Wild type H-ras and its mutant and wild type K-ras and its mutant showed varying degrees of cross hybridization between different probes and targets. The cross hybridization is frequently observed in reverse hybridization experiments and indicates insufficient stringency during the washing process after hybridization rather than any shortcoming of the immobilized oligonucleotide array.

Comparing the acyl fluoride activated polypropylene film with the ethylene acrylic acid copolymer and ethylene methacrylic acid copolymers of FIGS. 2–5 it is clear the small amount of background non-specific fluorescence is eliminated by impregnating the copolymer with carbon black.

EXAMPLE 5

The following describes preparing immobilized oligonucleotides utilizing inkjet printing technology to deliver controlled volumes of derivatized oligonucleotides to the solid support surface.

Figure 6:
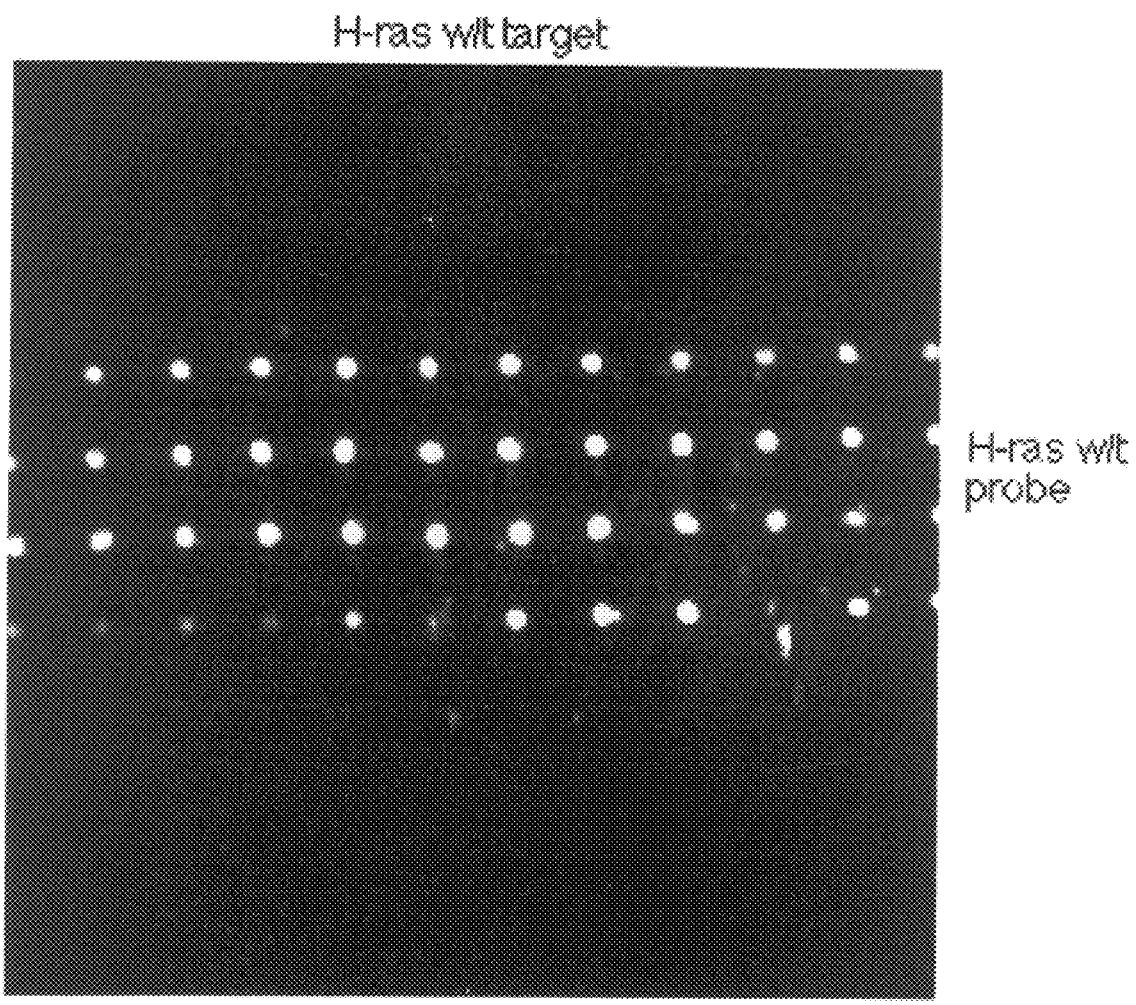
FIG. 6 shows CCD camera results obtained from the reverse hybridization of complementary H-ras oligonucleotides utilizing oligonucleotides immobilized onto acyl fluoride activated polypropylene by inkjet printing techniques.
Figure 7:
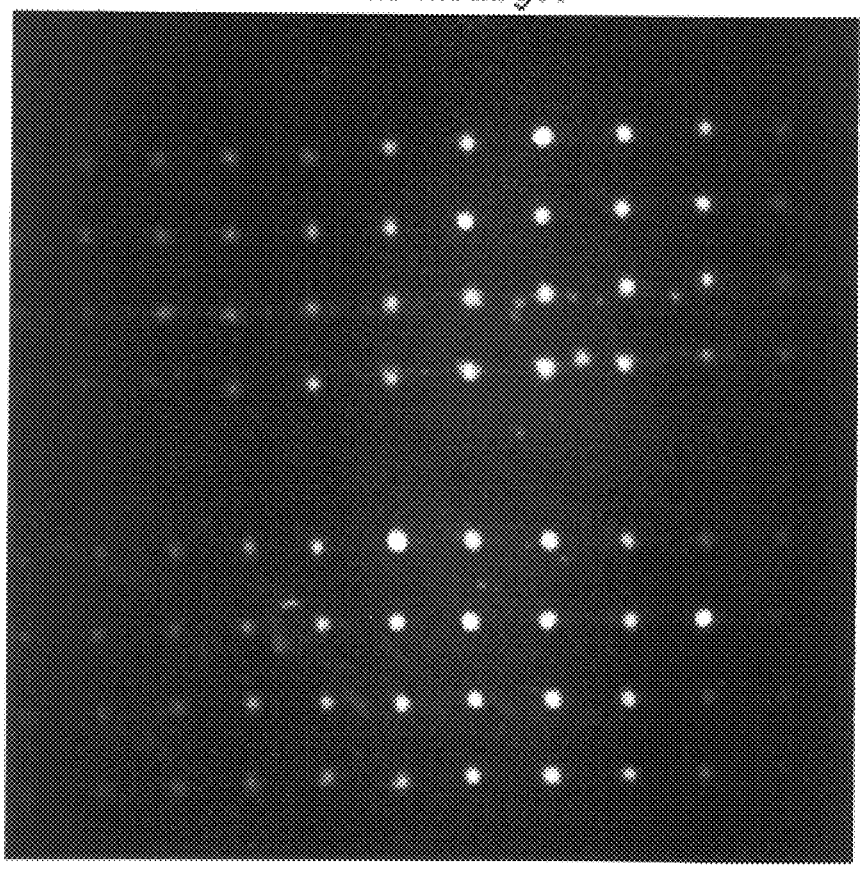
FIG. 7 shows CCD camera results obtained from the reverse hybridization of complementary H-ras oligonucleotides utilizing oligonucleotides immobilized onto acyl fluoride activated ethylene methacrylic acid copolymer solid support by inkjet printing techniques.

The H-ras wild type amino oligonucleotide probe prepared in Example 3 was dissolved in a solution of 5M $K_2CO_3$ to a concentration of approximately 200 pmol/$\mu$L. This solution was used to "print" spots onto acyl fluoride activated polypropylene prepared in Example 1 and acyl fluoride activated ethylene methacrylic acid copolymer prepared in Example 2. A Hewlett Packard HP2225C ThinkJet printer was used to deliver the spots which were each approximately 250 $\mu$m in diameter. After the individual elements or spots were delivered to the solid supports the residual carboxyl groups on the ethylene methacrylic acid copolymer solid support were converted to carboamides by washing the support with an aqueous solution of 30% ammonia. The resulting H-ras arrays were air dried and then exposed to the biotinylated wild type H-ras complementary oligonucleotides prepared as in Example 3. After washing the arrays containing the immobilized duplexes, the arrays were stained with streptavidin-Cy5 dye solution, washed and illuminated with a 650 nm diode laser. A charged coupled device camera collected the fluorescent emission at 680 nm. FIG. 6 and FIG. 7 show the results obtained by the CCD camera for the polypropylene activated solid support and the ethylene methacrylic acid copolymer solid support, respectively. Clearly, the inkjet printing technology combined with the biopolymer immobilizing reagents of the present invention provide appropriately sized array elements of sufficiently dense immobilized oligonucleotides.

EXAMPLE 6

Figure 8:
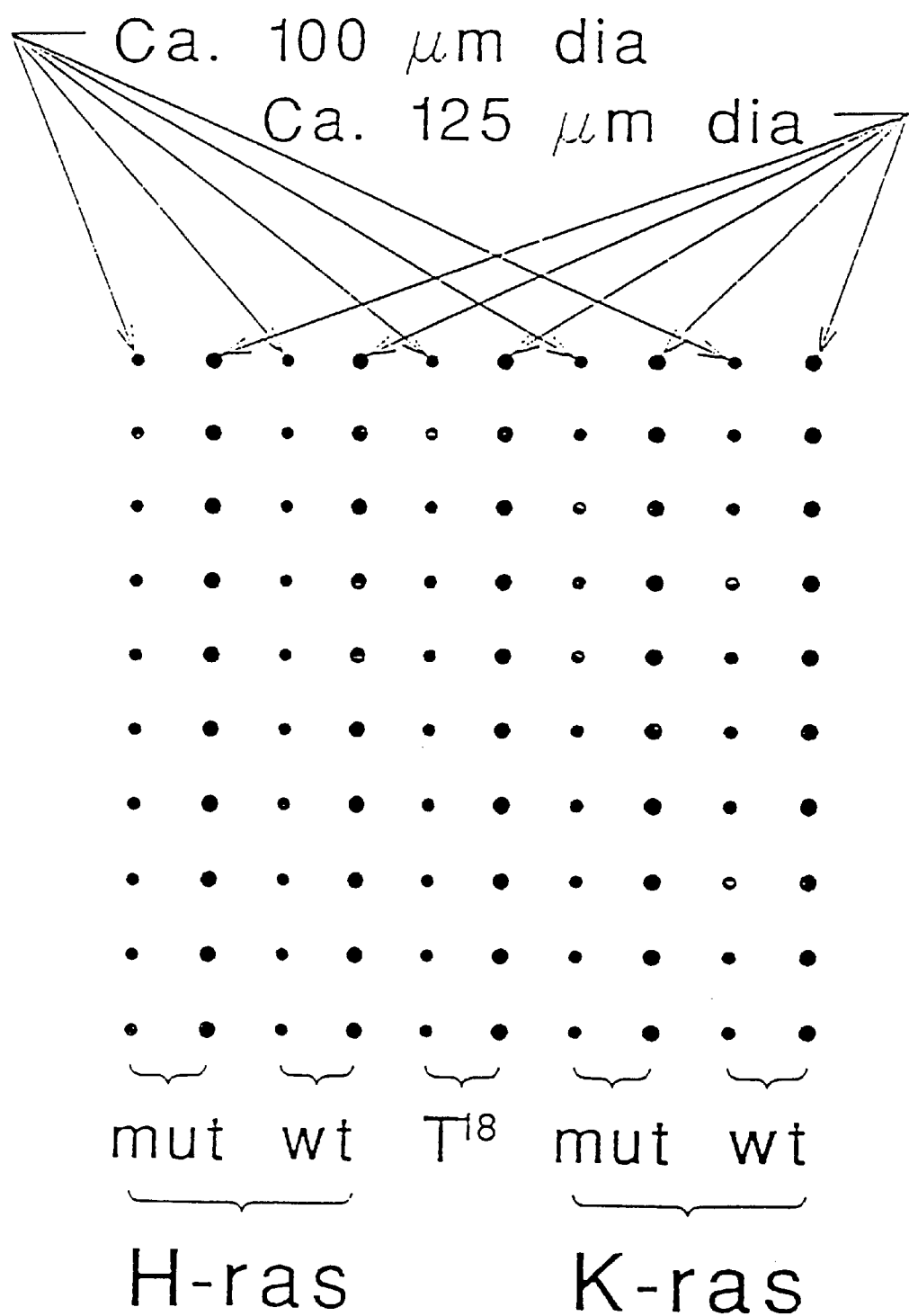
FIG. 8 graphically illustrates the general layout of oligonucleotide arrays immobilized utilizing piezo electric microjet printing techniques.

The following demonstrates the utility of the immobilizing reagents of the present invention in applications involving small areas of immobilized oligonucleotides for diagnostic purposes. A piezo electric microjet printing device available from MicroFab Technologies was used to deliver small volumes on the order of 80–160 pL of the amino derivatized oligonucleotide H-ras wild type and mutant probes, K-ras wild type and mutant probes, and a 5'$NH_2$ Poly-T probe. The general layout of the immobilized oligonucleotide arrays is graphically shown in FIG. 8. (Each probe was applied in duplicate rows, the first row being half the volume of the second row.) Duplicate rows of 5'-amino-poly-T were included in the middle of each array as a nonspecific control. The solid supports utilized in preparing the arrays were the acyl fluoride activated polypropylene prepared in Example 1 and carbon black-impregnated molded ethylene methacrylic acid strips prepared as described in Example 2. The printed spots were permitted to dry in place and then the solid supports having immobilized oligonucleotides were also washed as described in Example 3 with a 30% aqueous ammonia wash.

Figure 9:
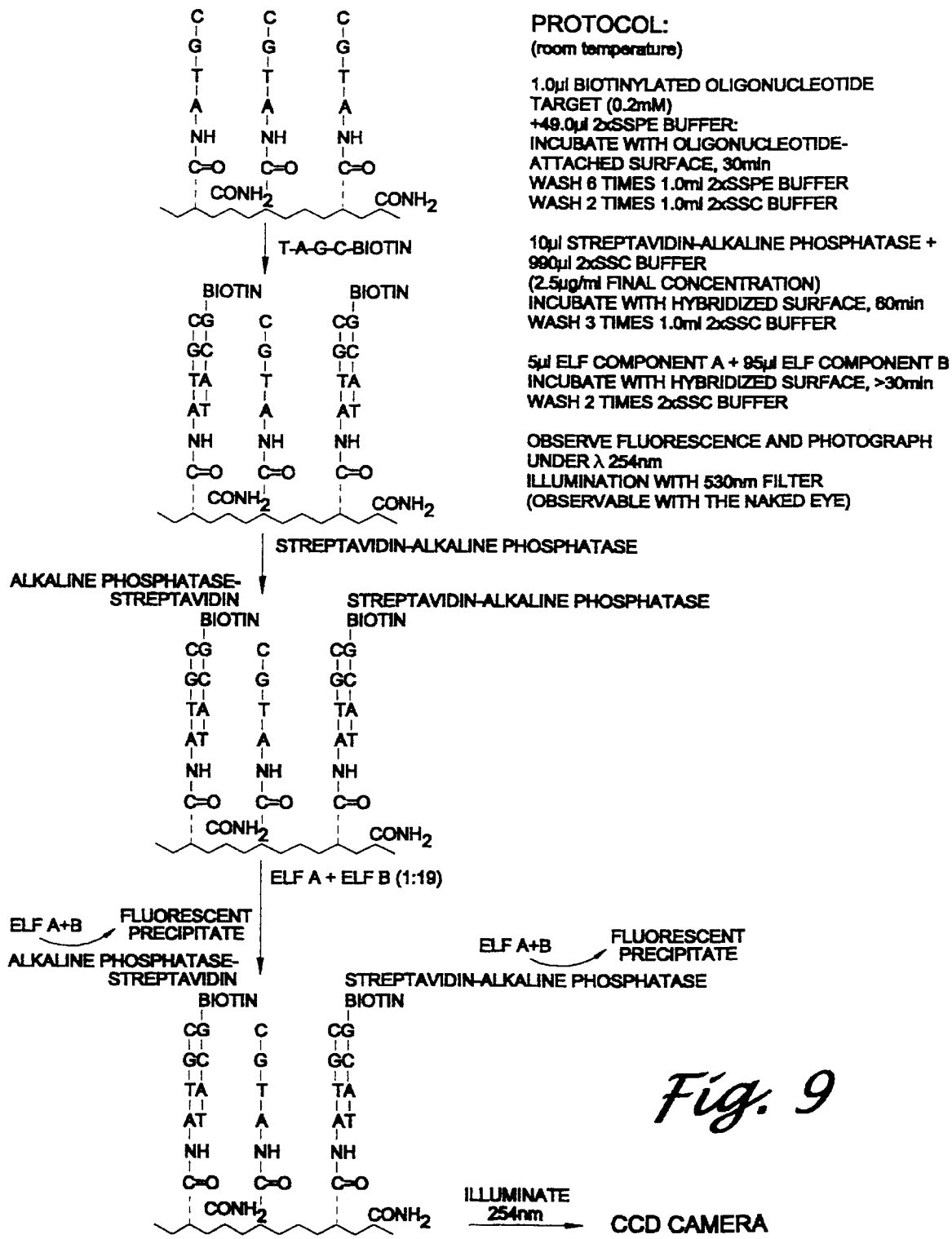
FIG. 9 is a flow chart indicating the general enzyme linked fluorescence technique utilized to detect hybridized oligonucleotides as shown in FIGS. 10–16.

All of the prepared arrays were contacted under hybridizing conditions with solutions of biotinylated oligonucleotide targets complementary to the immobilized probes as described. Following the hybridizing step the arrays were washed and then developed utilizing the enzyme linked fluorescence (ELF) technique which is shown graphically in the flow chart of FIG. 9. The fluorescent signals obtained from the ELF technique were visualized and recorded by a CCD camera equipped with a macro lens and 520 nm bandpass filter.

Figure 10:
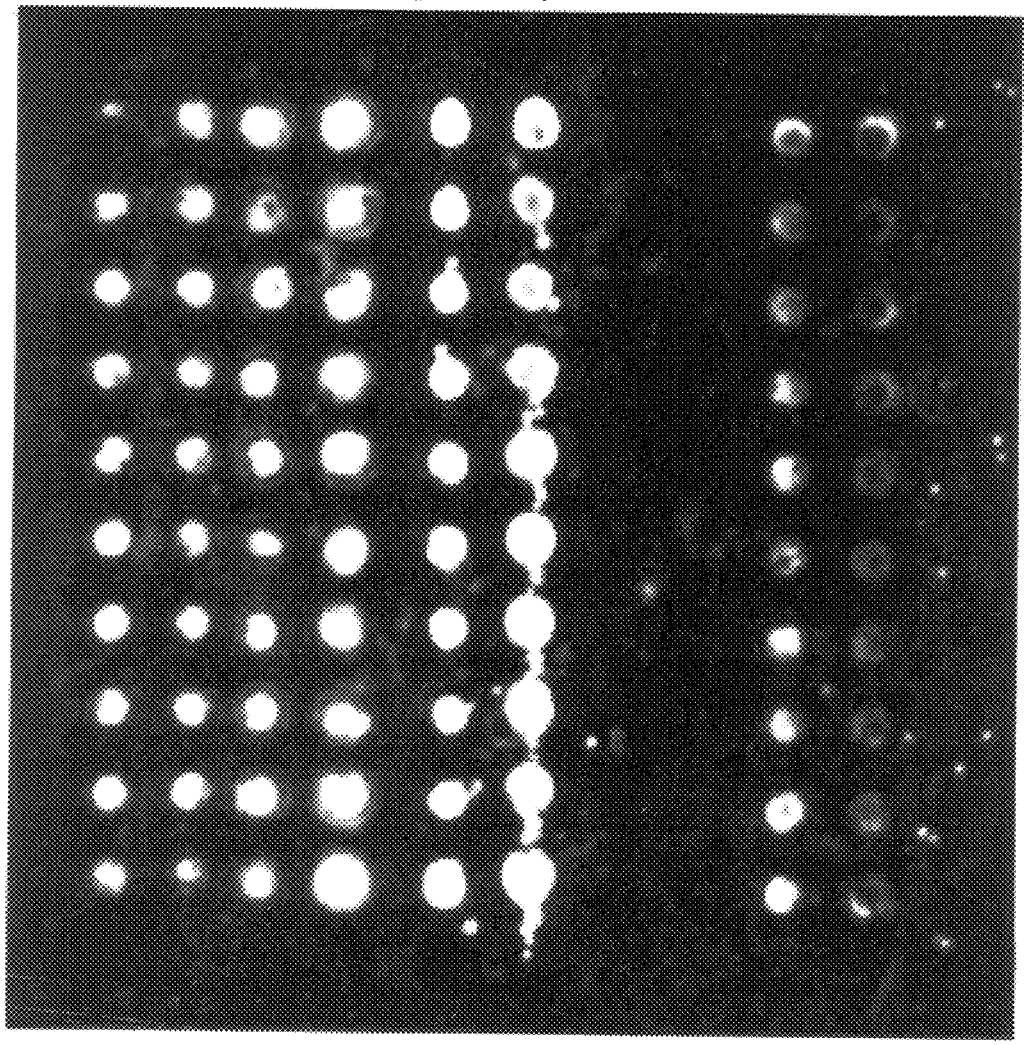
FIG. 10 shows CCD camera results obtained from the reverse hybridization of complementary H-ras, K-ras, and $A_{18}$ oligonucleotides with the probes immobilized onto acyl fluoride activated polypropylene film.
Figure 11:
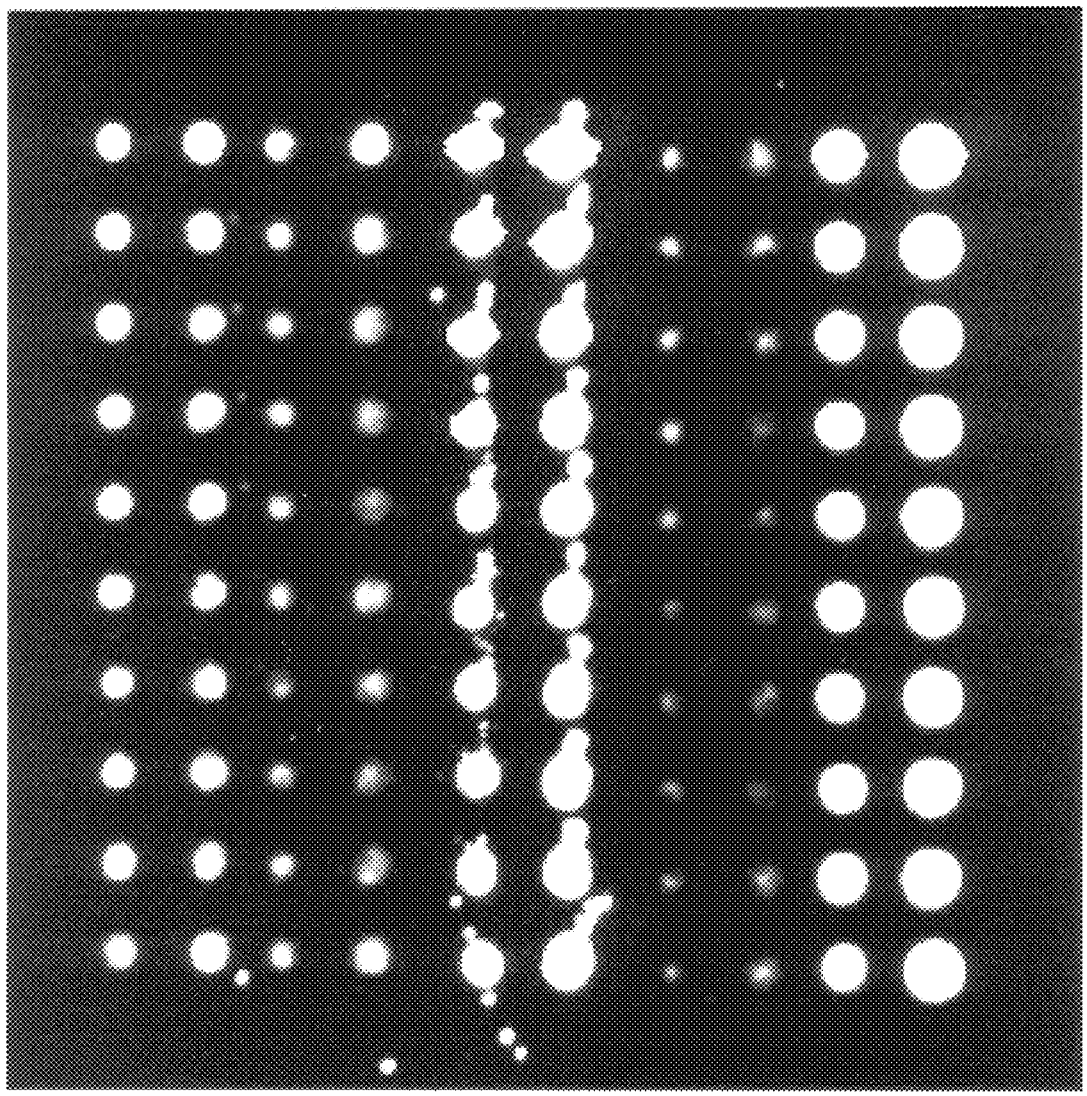
FIG. 11 shows CCD camera results obtained from the reverse hybridization of complementary H-ras, K-ras, and $A_{18}$ oligonucleotides with the probes immobilized onto acyl fluoride activated ethylene methacrylic acid strips impregnated with carbon black.

FIGS. 10–17 document the fluorescent emission observed by the CCD camera. FIGS. 10 and 11 illustrate results obtained utilizing the activated polypropylene film and activated ethylene methacrylic acid strips, respectively. These immobilization reagents were reverse hybridized with a mixture of all the biotinylated H-ras, biotinylated K-ras and biotinylated $A_{1\,8}$ oligonucleotide targets described in Example 3.

Figure 12:
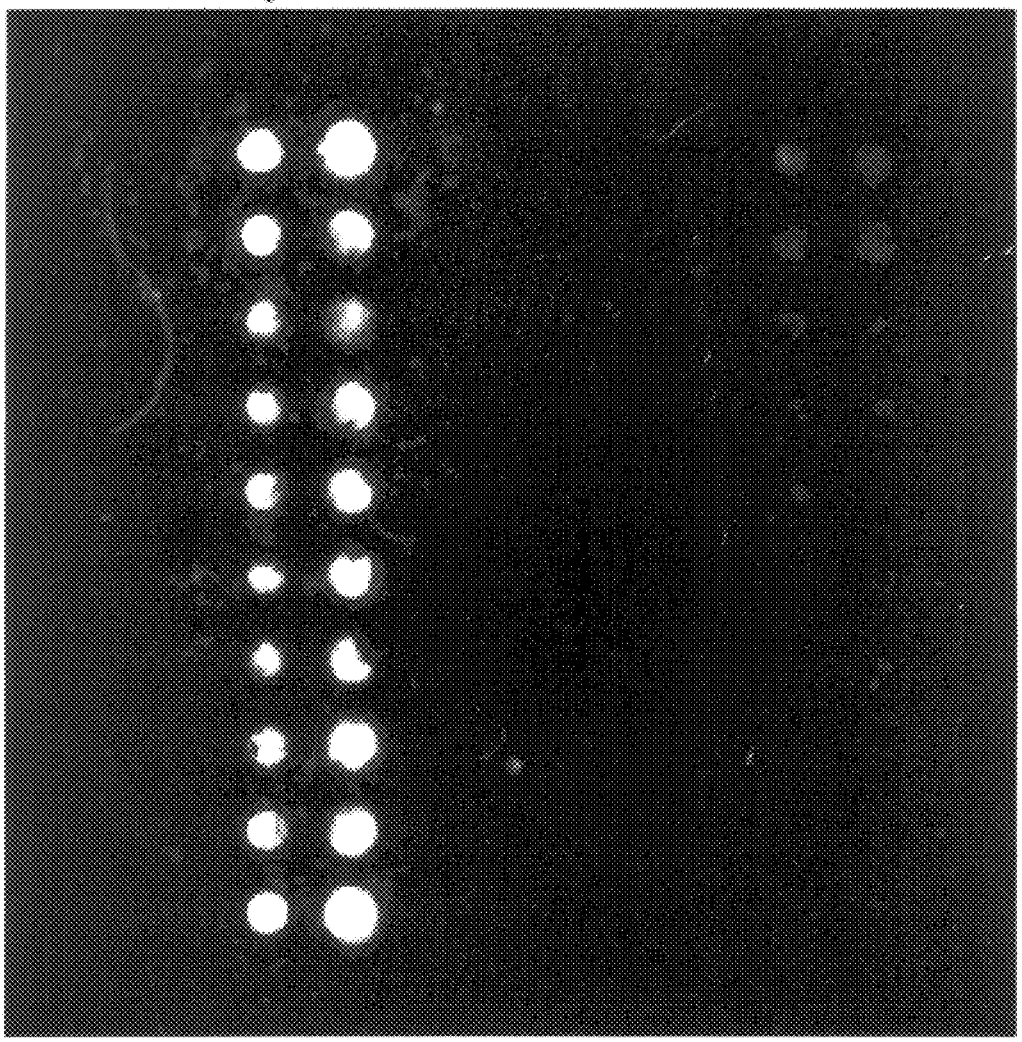
FIG. 12 shows CCD camera results obtained from the reverse hybridization of complementary H-ras wild type target oligonucleotides to H-ras, K-ras, and $T_{18}$ oligonucleotides immobilized onto acyl fluoride activated polypropylene film.
Figure 13:
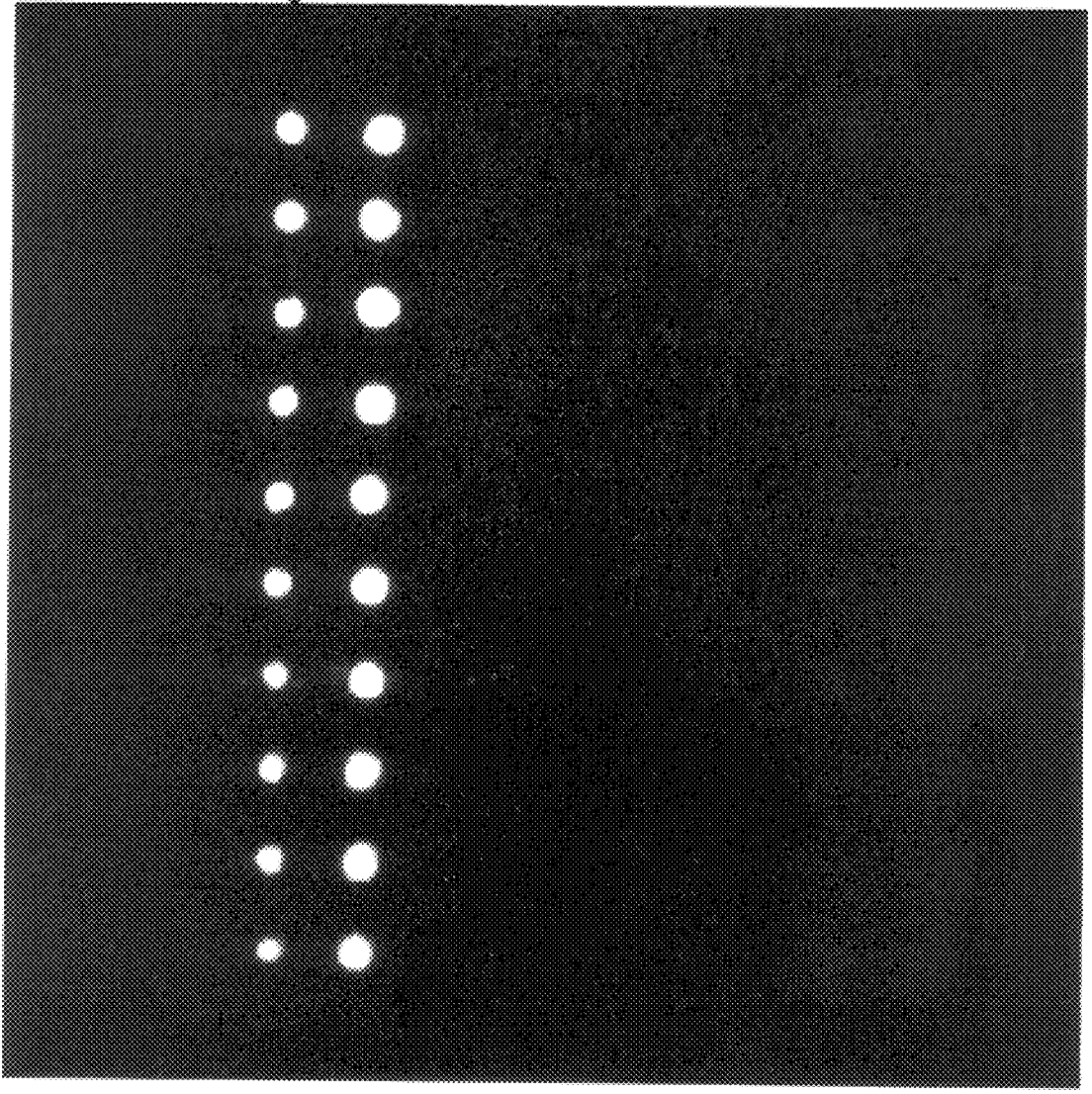
FIG. 13 shows CCD camera results obtained from the reverse hybridization of complementary H-ras target oligonucleotides to H-ras, K-ras, and $T_{18}$ oligonucleotides immobilized onto acyl fluoride activated ethylene methacrylic acid copolymer impregnated with carbon black.

FIGS. 12 and 13 show the CCD camera results obtained for reverse hybridization performed on oligonucleotides immobilized to activated polypropylene and activated ethylene methacrylic acid, respectively. Only biotinylated H-ras wild type targets were used in the reverse hydridization step. These results demonstrate the hybridization specificity obtained by the polypropylene immobilized oligonucleotides and the ethylene methacrylic acid copolymer immobilized oligonucleotides.

Figure 14:
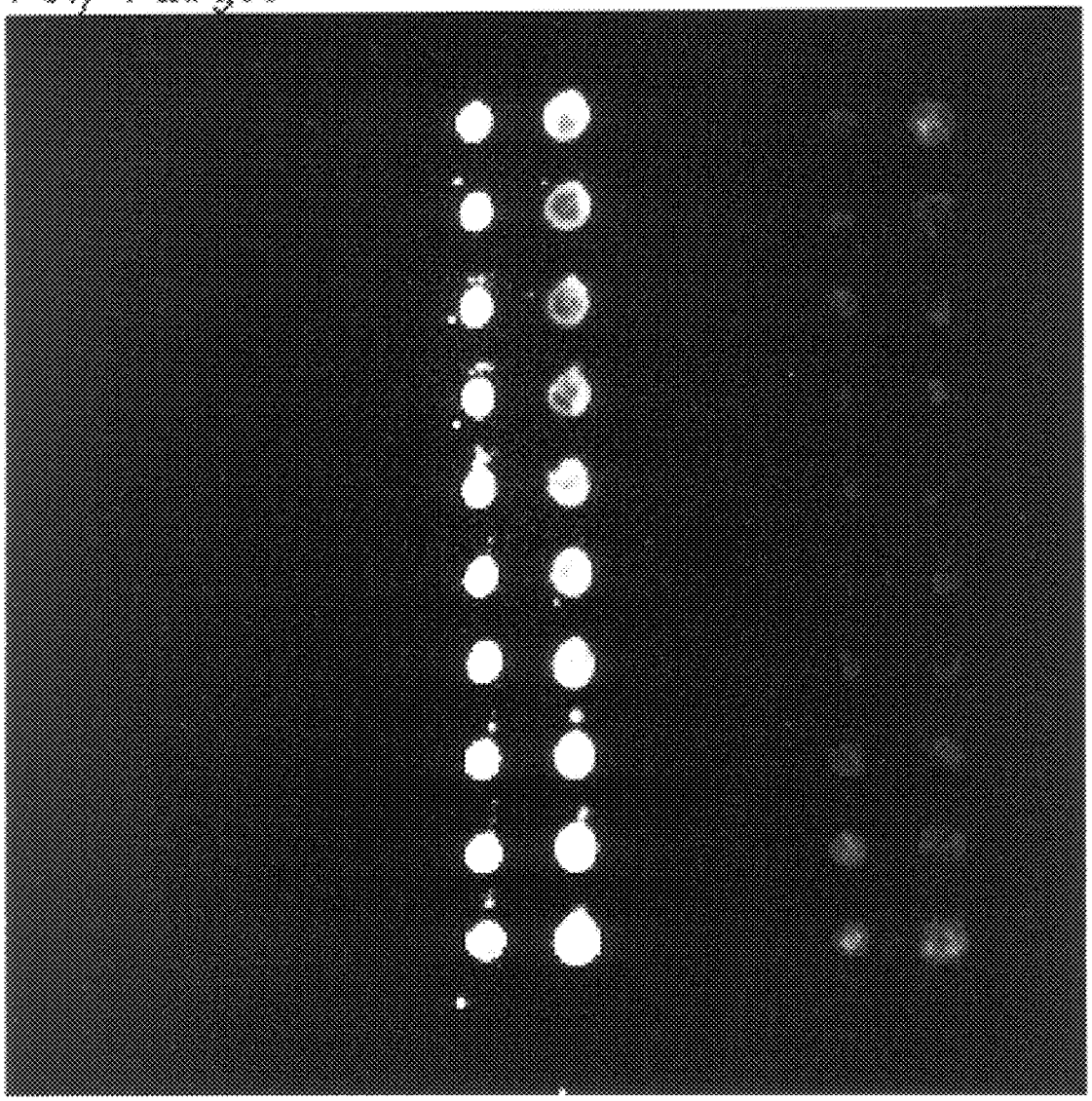
FIG. 14 shows CCD camera results obtained from the reverse hybridization of Poly-A targets to H-ras, K-ras, and $T_{18}$ oligonucleotides immobilized onto acyl fluoride activated polypropylene.
Figure 15:
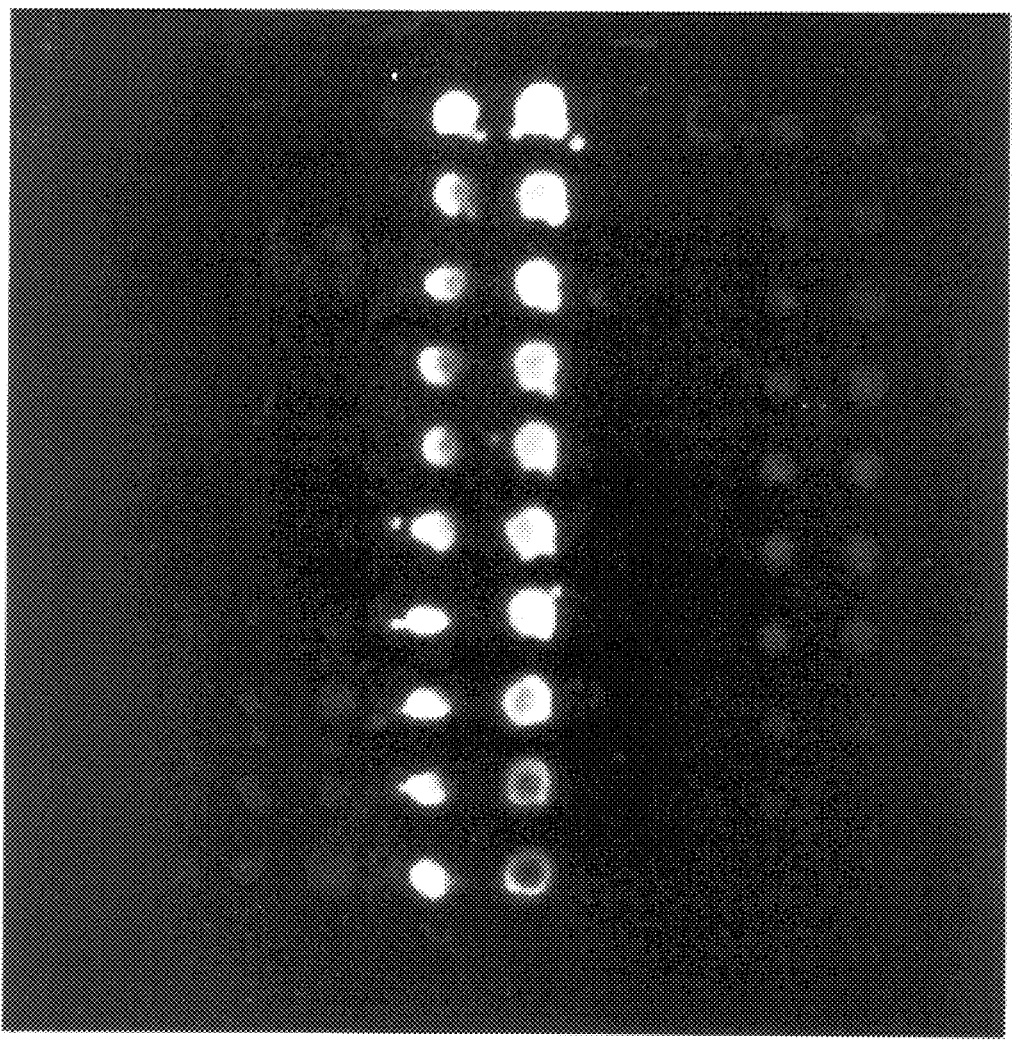
FIG. 15 shows CCD camera results obtained from the reverse hybridization of Poly-A target to H-ras, K-ras, and $T_{18}$ oligonucleotides immobilized onto acyl fluoride activated ethylene methacrylic acid impregnated with carbon black.

FIGS. 14 and 15 show the CCD camera results obtained with reverse hybridization using only biotinylated $A_{1\,8}$ target performed on oligonucleotides immobilized to activated polypropylene and activated ethylene methacrylic acid, respectively. These results further demonstrate the hybridization specificity obtained for the oligonucleotides immobilized on activated polypropylene and ethylene methacrylic acid copolymer.

Figure 16:
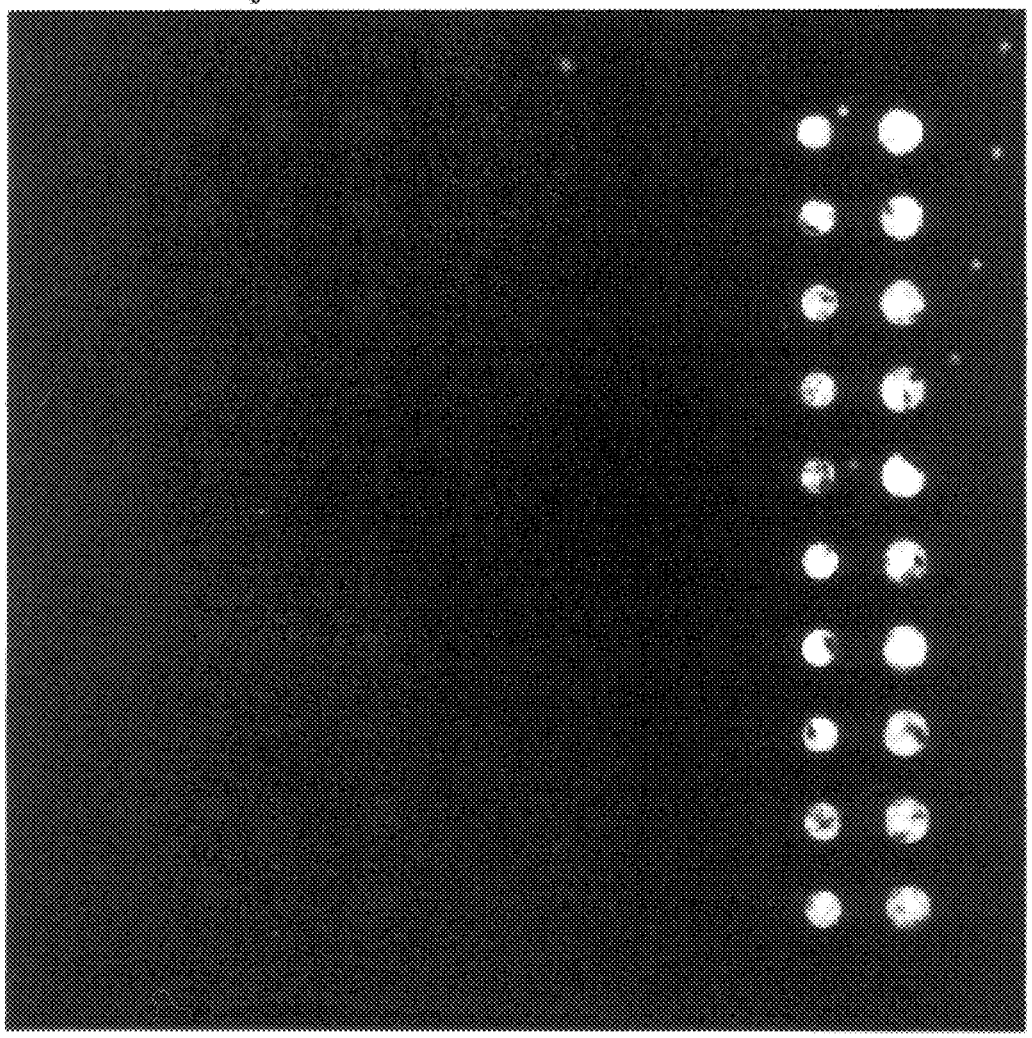
FIG. 16 shows CCD camera results obtained from the reverse hybridization of complementary K-ras wild type targets to H-ras, K-ras, and $T_{18}$ oligonucleotides immobilized onto acyl fluoride activated polypropylene.
Figure 17:
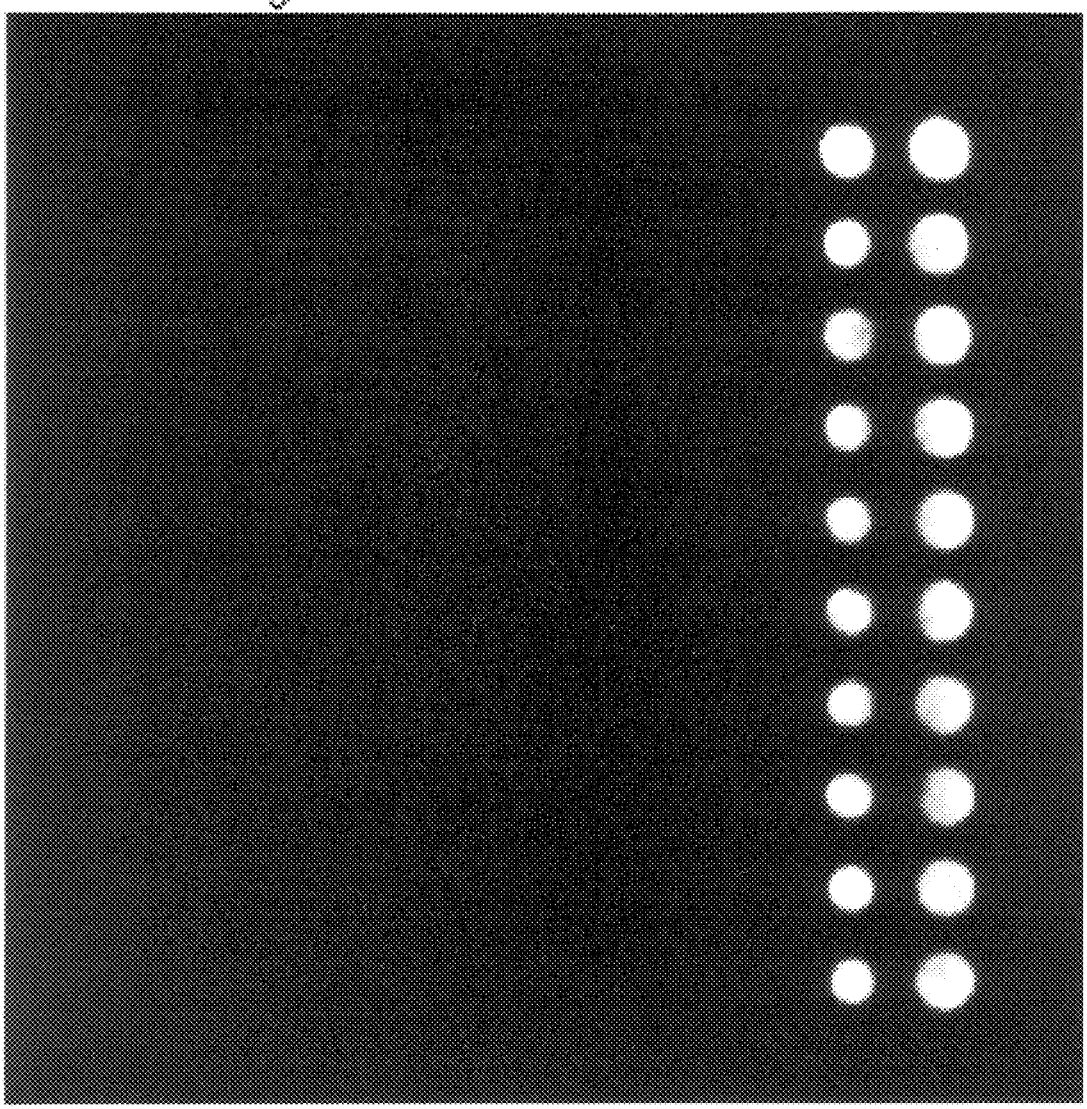
FIG. 17 shows CCD camera results obtained from the reverse hybridization of complementary K-ras wild type targets to H-ras, K-ras, and $T_{18}$ oligonucleotides immobilized onto acyl fluoride activated ethylene methacrylic acid copolymer.

FIGS. 16 and 17 show the CCD camera results obtained with reverse hybridization using only biotinylated K-ras wild type target performed on oligonucleotides immobilized to activated polypropylene and activated ethylene methacrylic acid, respectively. The results further demonstrate specificity of hybridization.

The foregoing clearly demonstrate that acyl fluoride activated polymer surfaces are advantageously useful for immobilizing oligonucleotides. Moreover, oligonucleotides immobilized on these surfaces are present in sufficiently high density and provide excellent hybridization specificity in reverse hybridization.

EXAMPLE 7

The following describes the direct synthesis of oligonucleotides utilizing a biopolymer synthesis reagent of the present invention. The reagent is a solid support film fabricated of ethylene acrylic acid copolymer and derivatized with a diamine to provide an amine terminated "linker".

To derivatize the copolymer, a film of ethylene acrylic acid copolymer obtained from Banner packaging was suspended in anhydrous diethyl ether containing greater than 5 fold excess of phosphorous. After approximately 16 hours at room temperature the film was removed from the phosphorous pentachloride mixture and washed with anhydrous diethyl ether and dichloromethane. This acyl chloride activated copolymer was then placed in a saturated solution of 1,12 diaminododecane in dichloromethane for about 16 hours. This reaction provides an amino terminated twelve methylene linker attached to the solid support with an amide attachment. It was determined that the density of amino groups on the film surface was approximately 100 $\mu$moles/cm$^2$ which is more than 100× that of prior art plasma aminated polypropylene film.

A sheet of the biopolymer synthesis reagent, approximately 8 cm×8 cm, was placed in an array maker (described in U.S. Pat. No. 5,429,807) and an array of cystic fibrosis oligonucleotides was synthesized using standard phosphoramidite synthetic methods.

The synthesized and immobilized cystic fibrosis array was developed utilizing the Invitrogen stain system which confirmed the presence of the immobilized array. Additionally, the synthesized cystic fibrosis array was incubated under hybridizing conditions with a biotinylated oligonucleotide which is complementary to one of the sequences represented in the cystic fibrosis array. Following the hybridization the resulting immobilized oligonucleotide duplex was brought into contact with a solution containing FITC-strepavidin purchased from ZYMED. The FITC was visualized confirming the successful reverse hybridization to appropriate elements of the synthesized and immobilized cystic fibrosis array.

EXAMPLE 8

The following describes the direct oligonucleotide synthesis onto a particulate solid support reagent of the present invention. Ethylene acrylic acid copolymer pellets purchased from Dow Chemical (Primacor #3460) were ground to a powder in a Waring blender. Five grams of the powder were placed in anhydrous diethylether containing an excess of phosphorous pentachloride. After 16 hours the copolymer powder was removed and washed with anhydrous diethyl ether and dichloromethane. This acid chloride derivatized powder was then placed in a saturated solution of 1,12 diaminododecane in dichloromethane for about 16 hours. This resulted in a particulate solid support synthesis reagent having an amino terminus and a twelve methylene length linker group. The linker is attached to the particulate polymer via an amide moiety.

The amino terminated particulate copolymer was then reacted with [(pentachlorophenyl)succinyl]nucleoside (DMT-T-CO(CH$_2$)$_2$-O-pcp) in pyridine and triethylamine for 2 days. This was followed by washing with pyridine, dichloromethane and pyridine and then air drying. This prepared solid support reagent was then sealed in a synthesis column sized for an Oligo 1000 automated DNA synthesizer (available from Beckman Instrument, Fullerton, Calif.). One of the cystic fibrosis oligonucleotides synthesized in Example 7 was synthesized according to standard phosphoramidite procedures provided by the manufacturer. During the synthesis normal dimethoxytrityl monitoring was observed following each deprotection step, indicating that normal synthesis was taking place.

EXAMPLE 9

The following demonstrate the direct synthesis of peptides onto a synthesis reagent of the present invention. Pellets of ethylene acrylic acid copolymer (Primacor #3460) were flattened into the shape of small disks about 5 mm in diameter. These disks were washed with methanol and dichloromethane and then suspended in anhydrous diethyl ether containing an approximately five fold excess of phosphorous pentachloride. After about 16 hours at room temperature the disks were removed from the phosphorous pentachloride mixture and washed with anhydrous diethyl ether and dichloromethane. The acyl chloride activated copolymer disks were then placed in a saturated solution of 1,12 diaminododecane in dichioromethane for about 16 hours. This reaction provides an amino terminated twelve methylene linker attached to the solid support disks with an amide attachment.

The activated disks were placed in a solution of bromoacetic anhydride and diisopropylcarbodiimide in 1:1 N-methylpyrrolidinone/dichloromethane and allowed to react for 2 hours. After washing the with N-methylpyrrolidinone, the disks were placed in a cysteamine saturated solution of 1:1 N-methylpyrrolidinone/dichloromethane for 2 hours to form an orthogonally cleavable thioether group.

This prepared ethylene acrylic acid copolymer solid support was then utilized to attach a glycine residue followed by synthesizing the CRISPP P12 epitope sequence by conventional Fmoc/t-Bu procedures. During the synthesis Kaiser ninhydrin tests showed coupled and N-terminally deprotected activity through the synthesis. Following trifluoroacetic acid (TFA) side-chain deprotection with 0.5 mL ethanedithiol scavenger and 9.5 mL TFA at room temperature for 5 hours and a standard workup, the synthesized peptide was specifically detected by immunoassay procedures with a horseradish peroxidase developer.

The foregoing demonstrated the utility of biopolymer immobilization and synthesis reagents of the present invention for peptide synthesis.

EXAMPLE 10

The following demonstrates the active ester activation of a suitably derivatized polypropylene film.

A 8×4 cm 0.5 mm thick strip of polypropylene film which had been previously plasma aminated as described above was washed 3 times with methanol, 3 times with acetonitrile and 3 times with isopropyl alcohol for 5 minutes each. After air drying, the strip was placed in an aqueous solution of 0.1 M NaHCO$_3$ and 0.1 M succinic anhydride. The solution and strip were shaken for about 16 hours and then washed with methanol and 3 times with isopropyl alcohol. After air drying, the strip was carboxylated by immersing it in 20 mL of acetic anhydride containing about 50 mg DMAP and shaking for 1 hour at room temperature.

The air dried carboxylated strip was then reacted with N-hydroxysuccinimde (Ref: Bodensky & Bodensky, *The Practice of Peptide Synthesis*) in 25 mL of dioxane containing 1.44 g hydroxysuccinimide and 2.58 g DCC (0.5 M each). The reaction was allowed to go for about 16 hours with shaking and then the strip was washed once with methanol, three times with a 1:1 solution of methanol and dichloromethane, and 3 times with acetonitrile. The strip was air dried and stored under argon.

The strip was split in two and on each strip an amino derivatized oligonucleotide was spotted. The oligonucleotide was derivatized using the Clontech Technologies derivatizing reagent and protocol described in Example 3.

On one strip the Invitrogen DNA version 3.0 DNA Dipstick was used to positively verify that DNA was immobilized. To the second strip a biotinylated DNA sequence complementary to the amino derivatized sequence was reverse hybridized to the strip using SPPE buffer for 1 hour at room temperature. Following the hybridization a solution of 25 μL strepavidin-FITC in 225 μL 2× SPPE buffer was placed over the strip. After the strepavidin was specifically complexed with the biotin the FITC was read utilizing a CCD camera. The results showed that the complementary target hybridized to the immobilized probe.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A reagent for immobilizing a biopolymer, the reagent comprising a solid support of a polymeric material having at least one planar, non-porous surface, the surface comprising pendant acyl fluoride functionalities.

2. The reagent of claim 1, where the polymeric material is selected from the group consisting of ethylene acrylic acid copolymers, ethylene methacrylic acid copolymers, and polypropylene.

3. The reagent of claim 1, where the polymeric material is a film.

4. A reagent for immobilizing a biopolymer, the reagent comprising a solid support of a polymeric material having at least one planar, non-porous surface, where the polymeric material is selected from the group consisting of acyl fluoride activated ethylene acrylic acid copolymers, and acyl fluoride activated derivatives of polypropylene.

5. The reagent of claim 4, where the polymeric material is a film.

6. A process for preparing a reagent for immobilizing a biopolymer, the process comprising the steps of:

providing a solid support of a polymeric material having at least one planar, non-porous surface; and activating the surface of the polymeric material by forming pendant acyl fluoride functionalities on the surface to provide an activated solid support.

7. The process of claim 6, where the polymeric material provided comprises pendant carboxyl functionalities.

8. The process of claim 6, where the polymeric material provided is selected from the group consisting of ethylene acrylic acid copolymers, ethylene methacrylic acid copolymers, and polypropylene.

9. The process of claim 6, where activating the surface further comprises reacting the surface of the solid support with a reagent selected from the group consisting of (diethylaminosulphur)trifluoride, cyanuric fluoride and tetramethylfluoroformadinium hexafluorophosphate.

10. The process of claim 6, further comprising derivatizing the polymeric material to form carboxyl functionalities prior to activating the surface.

11. The process of claim 10, where the polymeric material provided is aminated polypropylene, and where derivatizing the polymeric material to form carboxyl functionalities comprises reacting the aminated polypropylene with an anhydride.

12. The process of claim 6, where the solid support provided is a film.

13. A process for preparing a reagent for immobilizing a biopolymer, the process comprising the steps of:

providing a solid support of a polymeric material having at least one surface; and reacting the surface of the solid support with a reagent selected from the group consisting of (diethylaminosulphur)trifluoride, cyanuric fluoride and tetramethylfluoroformadinium hexafluorophosphate.

14. A process for preparing a reagent for immobilizing a biopolymer, the process comprising the steps of:

providing a solid support of a polymeric material having at least one surface;

forming carboxyl functionalities on the surface of the polymeric material; and converting the carboxyl functionalities to acyl fluoride functionalities.

* * * * *